US010421995B2

(12) United States Patent
Davis

(10) Patent No.: US 10,421,995 B2
(45) Date of Patent: Sep. 24, 2019

(54) HIGH SPEED MOLECULAR SENSING WITH NANOPORES

(71) Applicant: Genia Technologies, Inc., Mountain View, CA (US)

(72) Inventor: Randall Davis, Mountain View, CA (US)

(73) Assignee: GENIA TECHNOLOGIES, INC., Santa Clara, CA (US)

( * ) Notice: Subject to any disclaimer, the term of this patent is extended or adjusted under 35 U.S.C. 154(b) by 193 days.

(21) Appl. No.: 14/521,469

(22) Filed: Oct. 23, 2014

(65) Prior Publication Data

US 2015/0111779 A1 Apr. 23, 2015

Related U.S. Application Data

(60) Provisional application No. 61/894,577, filed on Oct. 23, 2013.

(51) Int. Cl.
*C12Q 1/68* (2006.01)
*C12Q 1/00* (2006.01)
*C12M 1/34* (2006.01)
*C12Q 1/6869* (2018.01)
*C12Q 1/6816* (2018.01)

(52) U.S. Cl.
CPC ......... *C12Q 1/6869* (2013.01); *C12Q 1/6816* (2013.01)

(58) Field of Classification Search
None
See application file for complete search history.

(56) References Cited

U.S. PATENT DOCUMENTS

| | | |
|---|---|---|
| 2,656,508 A | 10/1953 | Coulter |
| 4,121,192 A | 10/1978 | Wilson |
| 4,859,945 A | 8/1989 | Stokar |
| 5,198,543 A | 3/1993 | Blanco et al. |
| 5,302,509 A | 4/1994 | Cheeseman |
| 5,308,539 A | 5/1994 | Koden et al. |
| 5,457,342 A | 10/1995 | Herbst, II |
| 5,569,950 A | 10/1996 | Lewis et al. |
| 5,576,204 A | 11/1996 | Blanco et al. |
| 5,756,355 A | 5/1998 | Lang et al. |
| 5,770,367 A | 6/1998 | Southern et al. |
| 5,795,782 A | 8/1998 | Church et al. |
| 5,804,386 A | 9/1998 | Ju |
| 5,814,454 A | 9/1998 | Ju |
| 5,869,244 A | 2/1999 | Martin et al. |
| 5,876,936 A | 3/1999 | Ju |
| 5,912,155 A | 6/1999 | Chatterjee et al. |
| 5,939,301 A | 8/1999 | Hughes, Jr. et al. |
| 5,952,180 A | 9/1999 | Ju |
| 5,981,733 A | 11/1999 | Gamble et al. |
| 6,012,291 A | 1/2000 | Ema |
| 6,014,213 A | 1/2000 | Waterhouse et al. |
| 6,015,714 A | 1/2000 | Baldarelli et al. |
| 6,046,005 A | 4/2000 | Ju et al. |
| 6,082,115 A | 7/2000 | Strnad |
| 6,210,896 B1 | 4/2001 | Chan |
| 6,217,731 B1 | 4/2001 | Kane et al. |
| 6,232,103 B1 | 5/2001 | Short |
| 6,255,083 B1 | 7/2001 | Williams |
| 6,261,797 B1 | 7/2001 | Sorge et al. |
| 6,265,193 B1 | 7/2001 | Brandis et al. |
| 6,321,101 B1 | 11/2001 | Holmstrom |
| 6,362,002 B1 | 3/2002 | Denison et al. |
| 6,383,749 B2 | 5/2002 | Bochkariov et al. |
| 6,399,320 B1 | 6/2002 | Markau et al. |
| 6,399,335 B1 | 6/2002 | Kao et al. |
| 6,413,792 B1 | 7/2002 | Sauer |
| 6,485,703 B1 | 11/2002 | Cote et al. |
| 6,607,883 B1 | 8/2003 | Frey et al. |

(Continued)

FOREIGN PATENT DOCUMENTS

| | | |
|---|---|---|
| CN | 202 854 093 U | 4/2013 |
| JP | 2003527075 A | 9/2003 |

(Continued)

OTHER PUBLICATIONS

Schneider et al. DNA sequencing with nanopores. Nat Biotechnol. Apr. 10, 2012;30(4):326-8. doi: 10.1038/nbt.2181.
Seo, et al. Photocleavable fluorescent nucleotides for DNA sequencing on a chip constructed by site-specific coupling chemistry. Proc Natl Acad Sci USA. Apr. 13, 2004;101(15):5488-93. Epub Apr. 2, 2004.
Shim, et al. Encapsulating a single G-quadruplex aptamer in a protein nanocavity. J Phys Chem B. Jul. 17, 2008;112 (28):8354-60. Epub Jun. 19, 2008.
Simon, et al. Formation and stability of a suspended biomimetic lipid bilayer on silicon submicrometer-sized pores. J Colloid Interface Sci. Apr. 15, 2007;308(2):337-43. Epub Jan. 31, 2007.
Singer et al., Nanopore Based Sequence Specific Detection of Duplex DNA for Genomic Profiling, Jan. 8, 2010, published Jan. 20, 2010, pp. 738-742.

(Continued)

*Primary Examiner* — Maria G Leavitt
(74) *Attorney, Agent, or Firm* — FisherBroyles LLP; Victoria Brewster; Jason M. Pass

(57) ABSTRACT

Described herein are methods and devices for capturing and determining the identity of molecules using nanopores. The molecules can be counted, sorted and/or binned rapidly in a parallel manner using a large number of nanopores (e.g., 132,000 nanopores reading 180 million molecules in 1 hour). This fast capture and reading of a molecule can be used to capture probe molecules or other molecules that have been generated to represent an original, hard to detect molecule or portions of an original molecule. Precise counting of sample molecules or surrogates for sample molecules can occur. The methods and devices described herein can, among other things, replace flow cytometers and other counting instruments (e.g., while providing increased precision and throughput relative to a flow cytometer). In some cases, the devices and methods capture and hold particular molecules or surrogates of molecules in the nanopores and then eject them into clean solution to perform a capture, sorting, and binning function similar to flow cytometers.

9 Claims, 15 Drawing Sheets

(56) References Cited

U.S. PATENT DOCUMENTS

| | | |
|---|---|---|
| 6,616,895 B2 | 9/2003 | Dugas et al. |
| 6,627,748 B1 | 9/2003 | Ju et al. |
| 6,664,079 B2 | 12/2003 | Ju et al. |
| 6,673,615 B2 | 1/2004 | Denison et al. |
| 6,686,997 B1 | 2/2004 | Allen |
| 6,699,719 B2 | 3/2004 | Yamazaki et al. |
| 6,723,513 B2 | 4/2004 | Lexow |
| 6,746,594 B2 | 6/2004 | Akeson et al. |
| 6,762,048 B2 | 7/2004 | Williams |
| 6,794,177 B2 | 9/2004 | Markau et al. |
| 6,800,933 B1 | 10/2004 | Mathews et al. |
| 6,824,659 B2 | 11/2004 | Bayley et al. |
| 6,880,346 B1 | 4/2005 | Tseng et al. |
| 6,891,278 B2 | 5/2005 | Muller et al. |
| 6,916,665 B2 | 7/2005 | Bayley et al. |
| 6,952,651 B2 | 10/2005 | Su |
| 7,033,762 B2 | 4/2006 | Nelson et al. |
| 7,041,812 B2 | 5/2006 | Kumar et al. |
| 7,052,839 B2 | 5/2006 | Nelson et al. |
| 7,057,026 B2 | 6/2006 | Barnes et al. |
| 7,074,597 B2 | 7/2006 | Ju |
| 7,153,672 B1 | 12/2006 | Eickbush et al. |
| 7,189,503 B2 | 3/2007 | Akeson et al. |
| 7,223,541 B2 | 5/2007 | Fuller et al. |
| 7,229,799 B2 | 6/2007 | Williams |
| 7,233,541 B2 | 6/2007 | Yamamoto et al. |
| 7,238,485 B2 | 7/2007 | Akeson et al. |
| 7,244,602 B2 | 7/2007 | Frey et al. |
| 7,279,337 B2 | 10/2007 | Zhu |
| 7,321,329 B2 | 1/2008 | Tooyama et al. |
| 7,345,159 B2 | 3/2008 | Ju et al. |
| 7,361,466 B2 | 4/2008 | Korlach et al. |
| 7,368,668 B2 | 5/2008 | Ren et al. |
| 7,405,281 B2 | 7/2008 | Xu et al. |
| 7,446,017 B2 | 11/2008 | Liu et al. |
| 7,452,698 B2 | 11/2008 | Sood et al. |
| 7,622,279 B2 | 11/2009 | Ju |
| 7,622,934 B2 | 11/2009 | Hibbs et al. |
| 7,625,701 B2 | 12/2009 | Williams et al. |
| 7,626,379 B2 | 12/2009 | Peters et al. |
| 7,635,578 B2 | 12/2009 | Ju et al. |
| 7,710,479 B2 | 5/2010 | Nitta et al. |
| 7,713,698 B2 | 5/2010 | Ju et al. |
| 7,727,722 B2 | 6/2010 | Nelson et al. |
| 7,745,116 B2 | 6/2010 | Williams |
| 7,777,013 B2 | 8/2010 | Xu et al. |
| 7,777,505 B2 | 8/2010 | White et al. |
| 7,790,869 B2 | 9/2010 | Ju et al. |
| 7,871,777 B2 | 1/2011 | Schneider et al. |
| 7,883,869 B2 | 2/2011 | Ju et al. |
| 7,897,738 B2 | 3/2011 | Brandis et al. |
| 7,906,371 B2 | 3/2011 | Kim et al. |
| 7,924,335 B2 | 4/2011 | Itakura et al. |
| 7,939,259 B2 | 5/2011 | Kokoris et al. |
| 7,939,270 B2 | 5/2011 | Holden et al. |
| 7,947,454 B2 | 5/2011 | Akeson et al. |
| 7,948,015 B2 | 5/2011 | Rothberg et al. |
| 7,973,146 B2 | 7/2011 | Shen et al. |
| 7,989,928 B2 | 8/2011 | Liao et al. |
| 8,022,511 B2 | 9/2011 | Chiu et al. |
| 8,058,030 B2 | 11/2011 | Smith et al. |
| 8,058,031 B2 | 11/2011 | Xu et al. |
| 8,058,414 B2 | 11/2011 | Menchen et al. |
| 8,133,672 B2 | 3/2012 | Bjornson et al. |
| 8,137,569 B2 | 3/2012 | Harnack et al. |
| 8,148,516 B2 | 4/2012 | Williams et al. |
| 8,192,961 B2 | 6/2012 | Williams |
| 8,252,911 B2 | 8/2012 | Bjornson et al. |
| 8,257,954 B2 | 9/2012 | Clark et al. |
| 8,298,792 B2 | 10/2012 | Ju et al. |
| 8,324,914 B2 * | 12/2012 | Chen ............... C12Q 1/6816 |
| | | 324/713 |
| 8,541,849 B2 | 9/2013 | Chen et al. |
| 8,845,880 B2 * | 9/2014 | Davis ............. G01N 27/447 |
| | | 205/792 |
| 2003/0027140 A1 | 2/2003 | Ju et al. |
| 2003/0054360 A1 | 3/2003 | Gold et al. |
| 2003/0101006 A1 | 5/2003 | Mansky et al. |
| 2003/0166282 A1 | 9/2003 | Brown et al. |
| 2003/0198982 A1 | 10/2003 | Seela et al. |
| 2004/0122335 A1 | 6/2004 | Sackellares et al. |
| 2004/0185466 A1 | 9/2004 | Ju et al. |
| 2005/0032081 A1 | 2/2005 | Ju et al. |
| 2005/0091989 A1 | 5/2005 | Leija et al. |
| 2005/0127035 A1 | 6/2005 | Ling |
| 2005/0186576 A1 | 8/2005 | Chan et al. |
| 2005/0208574 A1 | 9/2005 | Bayley et al. |
| 2005/0221351 A1 | 10/2005 | Ryu |
| 2005/0239134 A1 | 10/2005 | Gorenstein et al. |
| 2006/0057565 A1 | 3/2006 | Ju et al. |
| 2006/0105461 A1 | 5/2006 | Tom-Moy et al. |
| 2006/0115951 A1 | 6/2006 | Mosley |
| 2006/0252038 A1 | 11/2006 | Ju |
| 2006/0278992 A1 | 12/2006 | Trezza et al. |
| 2007/0048745 A1 | 3/2007 | Joyce et al. |
| 2007/0173731 A1 | 7/2007 | Meka et al. |
| 2007/0190542 A1 | 8/2007 | Ling et al. |
| 2007/0196846 A1 | 8/2007 | Hanzel et al. |
| 2007/0275387 A1 | 11/2007 | Ju |
| 2008/0101988 A1 | 5/2008 | Kang et al. |
| 2008/0108082 A1 | 5/2008 | Rank et al. |
| 2008/0187915 A1 * | 8/2008 | Polonsky ............... B82Y 15/00 |
| | | 435/6.13 |
| 2008/0199932 A1 | 8/2008 | Hanzel et al. |
| 2008/0218184 A1 | 9/2008 | White et al. |
| 2008/0221806 A1 | 9/2008 | Bryant et al. |
| 2008/0286768 A1 | 11/2008 | Lexow |
| 2008/0318245 A1 | 12/2008 | Smirnov |
| 2009/0029477 A1 | 1/2009 | Meller et al. |
| 2009/0066315 A1 | 3/2009 | Hu et al. |
| 2009/0073293 A1 | 3/2009 | Yaffe et al. |
| 2009/0087834 A1 | 4/2009 | Lexow et al. |
| 2009/0099786 A1 | 4/2009 | Oliver et al. |
| 2009/0102534 A1 | 4/2009 | Schmid et al. |
| 2009/0136958 A1 * | 5/2009 | Gershow ............ C12Q 1/6825 |
| | | 435/6.13 |
| 2009/0167288 A1 | 7/2009 | Reid et al. |
| 2009/0215050 A1 | 8/2009 | Jenson |
| 2009/0263791 A1 | 10/2009 | Ju et al. |
| 2009/0269759 A1 | 10/2009 | Menchen et al. |
| 2009/0298072 A1 | 12/2009 | Ju |
| 2009/0325154 A1 | 12/2009 | Ju et al. |
| 2010/0025238 A1 | 2/2010 | Gottlieb et al. |
| 2010/0025249 A1 | 2/2010 | Polonsky et al. |
| 2010/0035260 A1 | 2/2010 | Olasagati et al. |
| 2010/0047802 A1 | 2/2010 | Bjornson et al. |
| 2010/0072080 A1 | 3/2010 | Karhanek et al. |
| 2010/0075328 A1 | 3/2010 | Bjornson et al. |
| 2010/0075332 A1 | 3/2010 | Patel et al. |
| 2010/0078777 A1 | 4/2010 | Barth et al. |
| 2010/0084276 A1 | 4/2010 | Lindsay |
| 2010/0092952 A1 | 4/2010 | Ju et al. |
| 2010/0093555 A1 | 4/2010 | Bjornson et al. |
| 2010/0121582 A1 | 5/2010 | Pan et al. |
| 2010/0122907 A1 | 5/2010 | Standford et al. |
| 2010/0148126 A1 | 6/2010 | Guan et al. |
| 2010/0243449 A1 | 9/2010 | Oliver |
| 2010/0261247 A1 | 10/2010 | Hanzel et al. |
| 2010/0267585 A1 | 10/2010 | Terbrueggen |
| 2010/0297644 A1 | 11/2010 | Kokoris et al. |
| 2010/0301398 A1 | 12/2010 | Rothberg et al. |
| 2010/0320094 A1 | 12/2010 | White et al. |
| 2010/0331194 A1 | 12/2010 | Turner et al. |
| 2011/0005918 A1 | 1/2011 | Akeson et al. |
| 2011/0014601 A2 | 1/2011 | Hardin et al. |
| 2011/0014611 A1 | 1/2011 | Ju et al. |
| 2011/0039259 A1 | 2/2011 | Ju et al. |
| 2011/0053284 A1 | 3/2011 | Meller et al. |
| 2011/0059505 A1 | 3/2011 | Hanzel et al. |
| 2011/0124518 A1 | 5/2011 | Cantor |
| 2011/0160093 A1 | 6/2011 | Van Den Boom et al. |
| 2011/0165652 A1 | 7/2011 | Hardin et al. |
| 2011/0168968 A1 | 7/2011 | Yang et al. |
| 2011/0174625 A1 | 7/2011 | Akeson et al. |

(56) References Cited

U.S. PATENT DOCUMENTS

| | | |
|---|---|---|
| 2011/0189659 A1 | 8/2011 | Clark et al. |
| 2011/0192723 A1 | 8/2011 | Chen et al. |
| 2011/0193249 A1 | 8/2011 | Chen et al. |
| 2011/0193570 A1 | 8/2011 | Chen et al. |
| 2011/0218414 A1 | 9/2011 | Kamath et al. |
| 2011/0244447 A1 | 10/2011 | Korlach |
| 2011/0287414 A1 | 11/2011 | Chen et al. |
| 2012/0034602 A1 | 2/2012 | Emig et al. |
| 2012/0040869 A1 | 2/2012 | Meller et al. |
| 2012/0052188 A1 | 3/2012 | Chen et al. |
| 2012/0094278 A1 | 4/2012 | Akeson et al. |
| 2012/0094332 A1 | 4/2012 | Lee et al. |
| 2012/0115736 A1 | 5/2012 | Bjornson et al. |
| 2012/0149021 A1 | 6/2012 | Yung et al. |
| 2012/0156680 A1 | 6/2012 | Ju et al. |
| 2012/0160687 A1 | 6/2012 | Akeson et al. |
| 2012/0160688 A1 | 6/2012 | Davis et al. |
| 2012/0187963 A1 | 7/2012 | Chen |
| 2012/0188092 A1 | 7/2012 | Chen |
| 2012/0196759 A1 | 8/2012 | Chen |
| 2012/0261261 A1 | 10/2012 | Huber |
| 2013/0015068 A1 | 1/2013 | Chen et al. |
| 2013/0040827 A1 | 2/2013 | MacEvicz |
| 2013/0203610 A1 | 8/2013 | Meller |
| 2013/0207205 A1 | 8/2013 | Chen |
| 2013/0237460 A1 | 9/2013 | Deierling et al. |
| 2013/0240359 A1 | 9/2013 | Turner et al. |
| 2013/0244340 A1 | 9/2013 | Davis et al. |
| 2013/0263946 A1 | 10/2013 | Afzali-Ardakani et al. |
| 2013/0264207 A1 | 10/2013 | Ju et al. |
| 2013/0327644 A1* | 12/2013 | Turner .................. C12Q 1/6874 204/543 |
| 2014/0014513 A1 | 1/2014 | Chen et al. |
| 2014/0034497 A1 | 2/2014 | Davis et al. |
| 2014/0093869 A1 | 4/2014 | Ju et al. |
| 2015/0119259 A1* | 4/2015 | Ju .................. C12Q 1/6869 506/2 |

FOREIGN PATENT DOCUMENTS

| | | |
|---|---|---|
| JP | 2006078491 | 3/2006 |
| JP | 2011501806 | 1/2011 |
| JP | 2011211905 | 10/2011 |
| WO | WO 91/06678 A1 | 5/1991 |
| WO | WO 93/21340 A1 | 10/1993 |
| WO | WO 97/32999 A1 | 9/1997 |
| WO | WO 97/46704 A1 | 12/1997 |
| WO | 2000056937 | 9/2000 |
| WO | WO 01/48235 A2 | 7/2001 |
| WO | WO 02/22883 A1 | 3/2002 |
| WO | WO 02/29003 A2 | 4/2002 |
| WO | WO 02/29003 A3 | 7/2002 |
| WO | WO 02/079519 A1 | 10/2002 |
| WO | WO 03/020734 A2 | 3/2003 |
| WO | WO 2004/007773 A1 | 1/2004 |
| WO | WO 2004/055160 A2 | 7/2004 |
| WO | WO 2004/055160 A3 | 8/2004 |
| WO | WO 2004/071155 A2 | 8/2004 |
| WO | WO 2004/072238 A2 | 8/2004 |
| WO | WO 2005/084367 A2 | 9/2005 |
| WO | WO 2005/084367 A2 | 12/2005 |
| WO | WO 2006/020775 A2 | 2/2006 |
| WO | WO 2007/002204 A2 | 1/2007 |
| WO | WO 2007/053702 A2 | 5/2007 |
| WO | WO 2007/053719 A2 | 5/2007 |
| WO | WO 2007/062105 A2 | 5/2007 |
| WO | WO 2007/127327 A2 | 11/2007 |
| WO | WO 2007/146158 A1 | 12/2007 |
| WO | WO 2007/053702 A3 | 1/2008 |
| WO | WO 2008/034602 A2 | 3/2008 |
| WO | WO 2008/069973 A2 | 6/2008 |
| WO | WO 2008/102120 A1 | 8/2008 |
| WO | WO 2008/124107 A1 | 10/2008 |
| WO | WO 2008/069973 A2 | 12/2008 |
| WO | WO 2008/034602 A3 | 2/2009 |
| WO | WO 2009/020682 A2 | 2/2009 |
| WO | WO 2007/002204 A3 | 4/2009 |
| WO | WO 2007/053719 A3 | 4/2009 |
| WO | WO 2007/062105 A3 | 4/2009 |
| WO | WO 2009/051807 A1 | 4/2009 |
| WO | WO 2009/054922 A1 | 4/2009 |
| WO | WO 2010/1109197 A2 | 9/2010 |
| WO | WO 2011/038241 A1 | 3/2011 |
| WO | WO 2011/067559 A1 | 6/2011 |
| WO | WO 2011/097028 A1 | 8/2011 |
| WO | WO 2011/106459 A2 | 9/2011 |
| WO | WO 2012/009578 A2 | 1/2012 |
| WO | 2012067911 | 5/2012 |
| WO | WO 2012/088339 A2 | 6/2012 |
| WO | WO 2012/088341 A2 | 6/2012 |
| WO | WO 2012/121756 A1 | 9/2012 |
| WO | WO 2013191793 * | 4/2013 |
| WO | WO 2013/109970 A1 | 7/2013 |
| WO | WO2013123450 A1 | 8/2013 |
| WO | WO 2013/154999 A2 | 10/2013 |
| WO | WO 2013/191793 A1 | 12/2013 |

OTHER PUBLICATIONS

Singh, et al. Synthesis of natural flutimide and analogous fully substituted pyrazine-2,6-diones, endonuclease inhibitors of influenza virus. J Org Chem. Aug. 10, 2001;66(16):5504-16.

Smith, et al. Overstretching B-DNA: the elastic response of individual double-stranded and single-stranded DNA molecules. Science. Feb. 9, 1996;271(5250):795-9.

Sood, et al. Terminal phosphate-labeled nucleotides with improved substrate properties for homogeneous nucleic acid assays. J Am Chem Soc. Mar. 2, 2005;127(8):2394-5.

Stanford, et al. Transport of DNA through a single nanometer-scale pore: evolution of signal structure. IEEE Workshop on Genomic Signal Processing and Statistics. Baltimore, MD. May 26, 2004.

Stanford, et al. Using HMMs to Quantify Signals from DNA Driven Through a Nanometer-Scale Pore. IEEE Workshop on Genomic Signal Processing and Statistics. Raleigh, NC. Oct. 2002; 11-13.

Stefureac, et al. Nanopore analysis of the interaction of metal ions with prion proteins and peptides. Biochem Cell Biol. Apr. 2010;88(2):347-58.

Stefureac, et al. Transport of alpha-helical peptides through alpha-hemolysin and aerolysin pores. Biochemistry. Aug. 1, 2006;45(30):9172-9.

Stoddart, et al. Nucleobase recognition in ssDNA at the central constriction of the alpha-hemolysin pore. Nano Lett. Sep. 8, 2010;10(9):3633-7.

Stoddart, et al. Single-nucleotide discrimination in immobilized DNA oligonucleotides with a biological nanopore. Proc Natl Acad Sci USA. May 12, 2009;106(19):7702-7. doi: 10.1073/pnas.0901054106. Epub Apr. 20, 2009.

Storm, et al. Translocation of double-strand DNA through a silicon oxide nanopore. Phys Rev E Stat Nonlin Soft Matter Phys. May 2005;71(5 Pt 1):051903. Epub May 6, 2005.

Streater, et al. Novel 3-hydroxy-2(1H)-pyridinones. Synthesis, iron(III)-chelating properties, and biological activity. J Med Chem. Jun. 19900;33(6): 1749-55.

Studer, et al. Formation of individual protein channels in lipid bilayers suspended in nanopores. Colloids Surf B Biointerfaces. Oct. 15, 2009;73(2):325-31. Epub Jun. 10, 2009.

Suzuki, et al. Highly reproducible method of planar lipid bilayer reconstitution in polymethyl methacrylate microfluidic chip. Langmuir. Feb. 14, 2006;22(4):1937-42.

Thomson et al. Preliminary nanopore cheminformatics analysis of aptamer-target binding strength. BMC Bioinformatics. Nov. 1, 2007;8 Suppl 7:S11.

Venkatesan, et al. Nanopore sensors for nucleic acid analysis. Nat Nanotechnol. Sep. 18, 2011;6(10):615-24. doi: 10.1038/nnano.2011.129.

Vercoutere, et al. Discrimination among individual Watson-Crick base pairs at the termini of single DNA hairpin molecules. Nucleic Acids Res. Feb. 15, 2003;31(4):1311-8.

(56) References Cited

OTHER PUBLICATIONS

Vercoutere, et al. Rapid discrimination among individual DNA hairpin molecules at single-nucleotide resolution using an ion channel. Nat Biotechnol. Mar. 2001; 19(3):248-52.
Viasnoff, et al. Probing DNA base pairing energy profiles using a nanopore. Eur Biophys J. Feb. 2009;38(2):263-9. Epub Oct. 3, 2008.
Wang, et al. DNA heterogeneity and phosphorylation unveiled by single-molecule electrophoresis. Proc Natl Acad Sci USA. Sep. 14, 20044;101(37):13472-7. Epub Sep. 1, 2004.
Wanunu, et al. DNA profiling using solid-state nanopores: detection of DNA-binding molecules. Nano Lett. Oct. 9, 2009(10):3498-502.
Weng, et al. Fluid biomembranes supported on nanoporous aerogel/xerogel substrates. Langmuir. Aug. 17, 2004;20 (17)1232-9.
Wilson, et al. Electronic control of DNA polymerase binding and unbinding to single DNA molecules. ACS Nano. Apr. 28, 2009;3(4):995-1003.
Wilson, et al. Feedback control of a DNA molecule tethered in a nanopore to repeatedly probe DNA-binding enzymes. Conf Proc IEEE Eng Med Biol Soc. 2008;2008:5745-8.
Winters-Hilt, et al. Nanopore-based kinetics analysis of individual antibody- channel and antibody-antigen interactions. BMC Bioinformatics. Nov. 1, 2007;8 Suppl 7:S20.
Woodside, et al. Direct measurement of the full, sequence-dependent folding landscape of a nucleic acid. Science. Nov. 10, 2006;314(5801):1001-4.
Woodside, et al. Nanomechanical measurements of the sequence-dependent folding landscapes of single nucleic acid hairpins. Proc Natl Acad Sci USA. Apr. 18, 2006;103(16):6190-5. Epub Apr. 10, 2006.
Wu, et al. Single-molecule detection of nitrogen mustards by covalent reaction within a protein nanopore. J Am Chem Soc. May 28, 2008;130(21):6813-9. Epub Apr. 30, 2008.
Zeineldin, et al. Using bicellar mixtures to form supported and suspended lipid bilayers on silicon chips. Langmuir. Sep. 12, 2006;22(19):8163-8.
Zwolak, et al. Electronic signature of DNA nucleotides via transverse transport. Nano Lett. Mar. 2005;5(3):421-4.
Akeson, et al. Microsecond time-scale discrimination among polycytidylic acid, polyadenylic acid, and polyuridylic acid as homopolymers or as segments within single RNA molecules. Biophys J. Dec. 1999;77(6):3227-33.
Aksimentiev, et al. Microscopic Kinetics of DNA Translocation through synthetic nanopores. Biophys J. Sep. 2004;87(3):2086-97.
Andersen. Sequencing and the single channel. Biophys J. Dec. 1999;77(6):2899-901.
Ashkenasy, et al. Recognizing a single base in an individual DNA strand: a step toward DNA sequencing in nanopores. Angew Chem Int Ed Engl. Feb. 18, 2005;44(9): 1401-4.
Atanasov, et al. Membrane on a chip: a functional tethered lipid bilayer membrane on silicon oxide surfaces. Biophys J. Sep. 2005;89(3):1780-8.
Baaken, et al. Planar microelectrode-cavity array for high-resolution and parallel electrical recording of membrane ionic currents. Lab Chip. Jun. 2008;8(6):938-44. Epub Apr. 16, 2008.
Bai, et al. Design and synthesis of a photocleavable biotinylated nucleotide for DNA analysis by mass spectrometry. Nucleic Acids Res. Jan. 26, 2004;32(2):535-41. Print 2004.
Benner, et al. Sequence-specific detection of individual DNA polymerase complexes in real time using a nanopore. Nat Nanotechnol. Nov. 2007;2(11 ):718-24. Epub Oct. 28, 2007.
Bezrukov, et al. Counting polymers moving through a single ion channel. Nature. Jul. 28, 1994;370(6487):279-81.
Bezrukov, et al. Dynamic partitioning of neutral polymers into a single ion channel. In NATO Advanced Research Workshop: Structure and dynamics of confined polymers. Kulwer Press. 2002; 117-130.
Bezrukov, et al. Dynamics and free energy of polymers partitioning into a nanoscale pore. Macromolecules. 1996; 29:8517-8522.
Bezrukov, et al. Neutral polymers in the nanopores of alamethicin and alphahemolysin. Biologicheskie Membrany 2001, 18, 451-455.
Boireau, et al. Unique supramolecular assembly of a redox protein with nucleic acids onto hybrid bilayer: towards a dynamic DNA chip. Biosens Bioelectron. Feb. 15, 2005;20(8):1631-7.
Bokhari, et al. A parallel graph decomposition algorithm for DNA sequencing with nanopores. Bioinformatics. Apr. 1, 2005;21(7):889-96. Epub Nov. 11, 2004.
Buchmann, et al. Electrochemical release from gold-thiolate electrodes for controlled insertion of ion channels into bilayer membrane. Bioorg Med Chem. Mar. 15, 2004;12(6):1315-24.
Butler, et al. Ionic current blockades from DNA and RNA molecules in the alpha-hemolysin nanopore. Biophys J. Nov. 1, 2007;93(9):3229-40. Epub Aug. 3, 2007.
Butler, et al. of RNA orientation during translocation through a biological nanopore. Biophys J. Jan. 1, 2006;90 (1):190-9. Epub Oct. 7, 2005.
Butler, et al. Single-molecule DNA detection with an engineered MspA protein nanopore. Proc Natl Acad Sci US A. Dec. 30, 2008;105(52):20647-52. Epub Dec. 19, 2008.
Chandler, et al. Membrane surface dynamics of DNA-threaded nanopores revealed by simultaneous single-molecule optical and ensemble electrical recording. Langmuir. Feb. 3, 2004;20(3):898-905.
Churbanov, et al. Duration learning for analysis of nanopore ionic current blockades. BMC Bioinformatics. Nov. 1, 2007;8 Suppl 7:S14.
Clarke, et al. Continuous base identification for single-molecule nanopore DNA sequencing. Nat Nanotechnol. Apr. 2009;4(4):265-70. Epub Feb. 22, 2009.
Cockroft, et al. A single-molecule nanopore device detects DNA polymerase activity with single-nucleotide resolution. J Am Chem Soc. Jan. 23, 2008;130(3):818-20. Epub Jan. 1, 2008.
Danelon, et al. Cell membranes suspended across nanoaperture arrays.Langmuir. Jan. 3, 2006;22(1):22-5.
Deamer, et al. Characterization of nucleic acids by nanopore analysis. Ace Chem Res. Oct. 2002;35(10):817-25.
Derrington, et al. Nanopore DNA sequencing with MspA. Proc Natl Acad Sci US A. Sep. 14, 2010;107 (37):16060-5. Epub Aug. 26, 2010.
Eid, et al. Real-time DNA sequencing from single polymerase molecules. Science. Jan. 2, 2009;323(5910):133-8. doi: 10.1126/science.I162986. Epub Nov. 20, 2008.
Einstein. Investigations on the theory of Brownian movement. Dover, New York 1956.
Ervin, et al. Simultaneous alternating and direct current readout of protein ion channel blocking events using glass nanopore membranes. Anal Chem. Mar. 15, 2008;80(6):2069-76. Epub Feb. 23, 2008.
Flusberg, et al. Direct detection of DNA methylation during single-molecule, real-time sequencing. Nat Methods. Jun. 2010;7(6):461-5. Epub May 9, 2010.
Fologea, et al. Detecting single stranded DNA with a solid state nanopore. Nano Lett. Oct. 2005;5(10):1905-9.
Fologea, et al. Slowing DNA translocation in a solid-state nanopore. Nano Lett. Sep. 2005;5(9): 1734-7.
Gu, et al. Stochastic sensing of organic analytes by a pore-forming protein containing a molecular adapter. Nature. Apr. 22, 1999;398(6729):686-90.
Guranowski, et al. Selective degradation of 2'-adenylated diadenosine tri- and tetraphosphates, Ap(3 )A and Ap ( 4 )A, by two specific human dinucleoside polyphosphate hydrolases. Arch Biochem Biophys. Jan. 1, 2000;373 (1):218-24.
Haas, et al. Improvement of the quality of self assembled bilayer lipid membrances by using a negative potential. Bioelectrochemistry. Aug. 2001;54(1 ): 1-10.
Halverson, et al. Asymmetric blockade of anthrax protective antigen ion channel asymmetric blockade. J Biol Chem. Oct. 7, 2005;280(40):34056-62. Epub Aug. 8, 2005.
Harlepp, et al. Probing complex RNA structures by mechanical force. Eur Phys J E Soft Matter. Dec. 2003;12 (4):605-15.
Heins, et al. Detecting single porphyrin molecules in a conically shaped synthetic nanopore. Nano Lett. Sep. 2005;5 (9):1824-9.

(56) References Cited

OTHER PUBLICATIONS

Heng, et al. Stretching DNA using the electric field in a synthetic nanopore. Nano Lett. Oct. 2005;5(10): 1883-8.
Heng, et al. The electromechanics of DNA in a synthetic nanopore. Biophys J. Feb. 1, 2006;90(3): 1098-106. Epub Nov. 11, 2005.
Henrickson, et al. Driven DNA transport into an asymmetric nanometer-scale pore. Phys Rev Lett. Oct. 2, 2000;85(14):3057-60.
Henrickson, et al. Probing single nanometer-scale pores with polymeric molecular rulers. J Chem Phys. Apr. 7, 2010;132(13):135101. doi: 10.1063/1.3328875.
Holden, et al. Direct introduction of single protein channels and pores into lipid bilayers. J Am Chem Soc. May 2005 11;127(18):6502-3.
Holden, et al. Direct transfer of membrane proteins from bacteria to planar bilayers for rapid screening by single-channel recording. Nat Chem Biol. Jun. 2006;2(6):314-8. Epub May 7, 2006.
Hromada, et al. Single molecule measurements within individual membrane-bound ion channels using a polymer-based bilayer lipid membrane chip. Lab Chip. Apr. 2008;8(4):602-8. Epub Feb. 29, 2008.
Ito, et al. Simultaneous determination of the size and surface charge of individual nanoparticles using a carbon nanotube-based Coulter counter. Anal Chem. May 15, 2003;75(10):2399-406.
Ju, et al. Cassette labeling for facile construction of energy transfer fluorescent primers. Nucleic Acids Res. Mar. 15, 1996;24(6):1144-8.
Ju, et al. Fluorescence energy transfer dye-labeled primers for DNA sequencing and analysis. Proc Natl Acad Sci USA. May 9, 1995;92(10):4347-51.
Ju, et al. Four-color DNA sequencing by synthesis using cleavable fluorescent nucleotide reversible terminators. Proc Natl Acad Sci US A. Dec. 26, 2006;103(52):19635-40. Epub Dec. 14, 2006.
Ju, et al. Energy transfer primers: a new fluorescence labeling paradigm for DNA sequencing and analysis. Nat Med. Feb. 1996;2(2):246-9.
Jurak, et al. Wettability and topography of phospholipid DPPC multilayers deposited by spin-coating on glass, silicon, and mica slides. Langmuir. Sep. 25, 2007;23(20):10156-63. Epub Aug. 28, 2007.
Kang, et al. A storable encapsulated bilayer chip containing a single protein nanopore. J Am Chem Soc. Apr. 18, 2007;129(15):4701-5. Epub Mar. 22, 2007.
Kasianowicz, et al. Characterization of individual polynucleotide molecules using a membrane channel. Proc Natl Acad Sci US A. Nov. 26, 1996;93(24):13770-3.
Kasianowicz. Nanopores: flossing with DNA. Nat Mater. Jun. 2004;3(6):355-6.
Kasianowicz. Nanometer-scale pores: potential applications for analyte detection and DNA characterization. Dis Markers. 2002;18(4):185-91.
Kasianowicz, et al. Physics of DNA threading through a nanometer pore and applications to simultaneous multianalyte sesnsing. In NATO Advanced Research Workshop: Structure and dynamics of confined polymers. Kluwer Press. 2002; 141-163.
Kasianowicz, et al. Simultaneous multianalysis detection with a nanopore. Anal. Chem. 2001; 73:2268-2272.
Kawano, et al. Controlling the translocation of single-stranded DNA through alpha-hemolysin ion channels using viscosity. Langmuir. Jan. 20, 2009;25(2): 1233-7.
Krasilnikov, et al. A simple method for the determination of the pore radius of ion channels in planar lipid bilayer membranes. FEMS Microbial Immunol. Sep. 1992;5(1-3):93-100.
Krasilnikov, et al. Single polymer molecules in a protein nanopore in the limit of a strong polymer-pore attraction. Phys Rev Lett. 2006; 97(1):018301. Epub Jul. 5, 2006.
Krasilnikov, et al. Sizing channels with neutral polymers. In NATO Advanced Research Workshop: Structure and dynamics of confined polymers. Kluwer Press. 2002; 97-116.
Kullman, et al. Transport of maltodextrins through maltoporin: a single-channel study. Biophys J. Feb. 2002;82 (2):803-12.
Kumar, et al. PEG-labeled nucleotides and nanopore detection for single molecule DNA sequencing by synthesis. Sci Rep. 2012;2:684. Epub Sep. 21, 2012.
Kumar, et al. Terminal phosphate labeled nucleotides: synthesis, applications, and linker effect on incorporation by DNA polymerases. Nucleosides Nucleotides Nucleic Acids. 2005;24(5-7):401-8.
Kutik, et al. Dissecting membrane insertion of mitochondrial beta-barrel proteins. Cell. Mar. 21, 2008;132(6):1011-24.
Lee, et al. Enhancing the catalytic repertoire of nucleic acids: a systematic study of linker length and rigidity. Nucleic Acids Res. Apr. 1, 2001;29(7): 1565-73.
Li, et al. A photocleavable fluorescent nucleotide for DNA sequencing and analysis. Proc Natl Acad Sci US A. Jan. 21, 2003;100(2):414-9. Epub Jan. 6, 2006.
Li, et al. Ion-beam sculpting at nanometre length scales. Nature. Jul. 12, 2001;412(6843): 166-9.
Linear Technology, High Efficiency Thermoelectric Cooler Controller, 2001.
Low Noise, Dual Switched Integrator, Burr-Brown Corporation, Sep. 1994.
Lundquist, et al. A new tri-orthogonal strategy for peptide cyclization. Org Lett. Sep. 19, 2002;4(19):3219-21.
Madampage, et al. Nanopore detection of antibody prion interactions. Anal Biochem. Jan. 1, 2010;396(1):36-41. Epub Aug. 21, 2009.
Mathe, et al. Nanopore unzipping of individual DNA hairpin molecules. Biophys J. Nov. 2004;87(5):3205-12. Epub Sep 3, 2004.
Mathe, et al. Orientation discrimination of single-stranded DNA inside the alpha-hemolysin membrane channel. Proc Natl Acad Sci USA. Aug. 30, 2005;102(35):12377-82. Epub Aug. 19, 2005.
Maurer, et al. Reconstitution of ion channels in agarose-supported silicon orifices. Biosens Bioelectron. May 15, 2007;22(11):2577-84. Epub Nov. 13, 2006.
McGuigan, et al. DNA fingerprinting by sampled sequencing. Methods in Enzymology. 1993; 218:241-258.
McNally, et al. Optical recognition of converted DNA nucleotides for single-molecule DNA sequencing using nanopore arrays. Nano Lett. Jun. 9, 2010;10(6):2237-44.
Meller, et al. Rapid nanopore discrimination between single polynucleotide molecules. Proc Natl Acad Sci US A. Feb. 1, 2000;97(3):1079-84.
Meller, et al. Single molecule measurements of DNA transport through a nanopore. Electrophoresis. Aug. 2002;23 (16):2583-91.
Mohammad, et al. Controlling a single protein in a nanopore through electrostatic traps. J Am Chem Soc. Mar. 26, 2008;130(12):4081-8. Epub Mar. 6, 2008.
Movileanu, et al. Partitioning of a polymer into a nanoscopic protein pore obeys a simple scaling law. Proc Natl Acad Sci USA. Aug. 28, 2001;98(18):10137-41. Epub Aug. 14, 2001.
Movileanu, et al. Partitioning of individual flexible polymers into a nanoscopic protein pore. Biophys J. Aug. 2003;85 (2):897-910.
Mulder, et al. Nucleotide modification at the gamma-phosphate leads to the improved fidelity of HIV-1 reverse transcriptase. Nucleic Acids Res. Sep. 1, 2005;33(15):4865-73. Print 2005.
Nakane, et al. A Nanosensor for Transmembrane Capture and Identification of Single Nucleic Acid Molecules, Biophysical Journal, vol. 87, Issue 1, Jul. 2004, pp. 615-621, ISSN 0006-3495.
Oxford Nanopore Technologies, Sensor Array Chip, Jul. 14, 2011.
Park, et al. DNA hybridization sensors based on electrochemical impedance spectroscopy as a detection tool. Sensors (Basel). 2009;9(12):9513-32. Epub Nov. 26, 2009.
Perkins, et al. Relaxation of a single DNA molecule observed by optical microscopy. Science. May 6, 1994;264 (5160):822-6.
Pourmand, et al. Multiplex Pyrosequencing. Acids Res. Apr. 1, 2002;30(7):e31.
Purnell, et al. Discrimination of single base substitutions in a DNA strand immobilized in a biological nanopore. ACS Nano. Sep. 22, 2009;3(9):2533-8.
Reiner, et al. Temperature sculpting in yoctoliter volumes. J Am Chem Soc. Feb. 27, 2013;135(8):3087-94. doi: 10.1021/ja309892e. Epub Feb. 14, 2013.

(56) References Cited

OTHER PUBLICATIONS

Reiner, et al. Theory for polymer analysis using nanopore-based single-molecule mass spectrometry. Proc Natl Acad Sci USA. Jul. 6, 2010;107(27): 12080-5. doi: 10.1073/pnas.1002194107. Epub Jun. 21, 2010.

Reynolds, et al. Synthesis and stability of novel terminal phosphate-labeled nucleotides. Nucleosides Nucleotides Nucleic Acids. Jan. 2008;27(1 ): 18-30. doi: 10.1080/15257770701571768.

Rief, et al. Sequence-dependent mechanics of single DNA molecules. Nat Struct Biol. Apr. 1999;6(4):346-9.

Robertson, et al. Single-molecule mass spectrometry in solution using a solitary nanopore. Proc Natl Acad Sci USA. 2007;104(20):8207-11. Epub May 9, 2007.

Rosenblum, et al. New dye-labeled terminators for improved DNA sequencing patterns. Nucleic Acids Res. Nov. 15, 1997;25(22):4500-4.

Rosenstein, et al. Integrated nanopore sensing platform with sub-microsecond temporal resolution. Nat Methods. Mar. 18, 2012;9(5):487-92. doi: 10.1038/nmeth.1932.

Rostovtsev, et al. A stepwise huisgen cycloaddition process: copper(I)-catalyzed regioselective "ligation" of azides and terminal alkynes. Angew Chem Int Ed Engl. Jul. 15, 2002;41(14):2596-9.

Rotem et al., Temperature Measurement in the Intel Core Duo Processor, 2007.

Saleh, et al. Direct detection of antibody-antigen binding using an on-chip artificial pore. Proc Natl Acad Sci USA. Feb. 4, 2003;100(3):820-4. Epub Jan. 27, 2003.

Sanchez-Magraner, et al. Membrane insertion of *Escherichia coli* alpha-hemolysin is independent from membrane lysis. J Biol Chem. Mar. 3, 2006;281(9):5461-7. Epub Dec. 22, 2005.

Sauer-Budge, et al. Unzipping kinetics of double-stranded DNA in a nanopore. Phys Rev Lett. Jun. 13, 2003;90 (23):238101. Epub Jun. 9, 2003.

\* cited by examiner

HIGH SPEED MOLECULAR SENSING WITH NANOPORES

CROSS-REFERENCE TO RELATED APPLICATIONS

This application claims the benefit of U.S. Provisional Application No. 61/894,577, filed on Oct. 23, 2013, which is incorporated by reference herein in its entirety.

BACKGROUND

Some applications in genomic analysis require the detection of copy number variation. Pre-natal screening, for example, may determine if certain portions of Chromosome 13, 19, and 21 are duplicated or deleted in fetal free floating deoxyribonucleic acid (DNA). One way to accomplish this is to enrich a whole genome sample for the specific regions on the select chromosomes (e.g., via PCR). PCR however can introduce bias or errors in the product in several different ways, including disparities between the rates of enzymes or differences between primer binding affinities to particular sites.

BRIEF SUMMARY OF THE INVENTION

Described herein are methods, devices and systems for capturing and determining the identity of molecules using nanopores. The molecules can be counted, sorted and/or binned rapidly in a parallel manner using a large number of nanopores (e.g., 132,000 nanopores reading 180 million molecules in 1 hour). This fast capture and reading of a molecule can be used to capture probe molecules or other molecules that have been generated to represent an original, hard to detect molecule or portions of an original molecule. This can be used, for example, in the detection of nucleic acid (e.g., DNA) polymorphisms, such as copy number variation. Precise counting of sample molecules or surrogates for sample molecules can occur. The methods and devices described herein can, among other things, replace flow cytometers and other counting instruments (e.g., while providing increased precision and throughput relative to a flow cytometer). In some cases, the devices and methods capture and hold particular molecules or surrogates of molecules in the nanopores and then eject them into clean solution to perform a capture, sorting, and binning function similar to flow cytometers.

In an aspect, the disclosure provides a method for molecular counting and/or sorting, comprising: (a) providing an array of nanopores, wherein an individual nanopore of said array is individually addressable by an adjacent sensing electrode; (b) providing a plurality of markers that each comprise nucleotides, wherein at least two of the nucleotides hybridize with a nucleic acid sample, and wherein the markers are capable of being captured by the individual nanopore and identified using the sensing electrode; and (c) capturing and identifying the markers with the array of nanopores at a rate of at least about 1 marker per second per nanopore.

In some embodiments, the sensing electrode is operated in Faradaic mode.

In some embodiments, the sensing electrode is operated in non-Faradaic mode.

In some embodiments, the nucleic acid sample is derived from a patient.

In another aspect, the disclosure provides a method for molecular counting and/or sorting, comprising: (a) providing an array of nanopores, wherein an individual nanopore of said array is individually addressable by an adjacent sensing electrode operated in non-faradaic mode; (b) providing a plurality of markers capable of being captured by the individual nanopore and identified using the sensing electrode; and (c) capturing and identifying the markers with the array of nanopores at a rate of at least about 1 marker per second per nanopore.

In some embodiments, the markers are captured and identified at a rate of at least about four markers per second per nanopore.

In some embodiments, the plurality of markers comprise at least four different markers.

In some embodiments, the markers comprise tails having at least four different lengths.

In some embodiments, the markers are identified based on a voltage at which the markers leave the nanopore.

In some embodiments, the method further comprises releasing the captured markers from the nanopore.

In some embodiments, the plurality of markers comprise markers to be sorted, wherein the markers to be sorted are captured, identified and held in the nanopores, and wherein markers other than the markers to be sorted are captured, identified and released from the nanopores.

In some embodiments, the markers to be sorted are released as a group and collected.

In some embodiments, the markers to be sorted are released as a group when the ratio of the number of markers to be sorted divided by a remaining number of markers that are captured and identified by the nanopores increases above a threshold.

In some embodiments, the method further comprises quantifying markers that comprise less than about 0.05% of the total number of markers.

In some embodiments, wherein said capturing and identifying comprises capturing and identifying at least about 1 million markers per hour.

In some embodiments, the rate is at least about 100 million markers per hour.

In some embodiments, the rate is at least about 1 billion markers per hour.

In some embodiments, said capturing and identifying comprises counting and/or sorting at least about 8 different types of markers.

In some embodiments, said capturing and identifying comprises counting and/or sorting at least about 32 different types of markers.

In some embodiments, said capturing and identifying comprises counting and/or sorting at least about 100 different types of markers.

In some embodiments, said capturing and identifying comprises counting and/or sorting at least about 500 different types of markers.

In some embodiments, said capturing and identifying comprises counting and/or sorting at least about 500 different types of markers In some embodiments, the array of nanopores is configured to have a plurality of regions capable of performing the method on different samples.

In some embodiments, the markers are identified based on a current that flows through the individual nanopore and/or a voltage at which the marker leaves the nanopore.

In some embodiments, the markers each comprise a single stranded nucleic acid molecule attached to a bead.

In some embodiments, the markers are generated by: (a) hybridizing a first probe to the nucleic acid sample; (b) hybridizing a second probe to the nucleic acid sample adjacent to the first probe; (c) ligating the first probe to the second probe to produce a combined probe; and (d) capturing the combined probe with a bead attached to an oligonucleotide, wherein the oligonucleotide hybridizes with the combined probe.

In some embodiments, the method further comprises determining copy number variation of a nucleic acid sequence in the nucleic acid sample.

In some embodiments, the method further comprises detecting differences in copy number that are less than or equal to about 0.05%.

In some embodiments, the method further comprises quantifying relative RNA expression levels in the nucleic acid sample.

In some embodiments, the method further comprises performing an ELISA assay on the nucleic acid sample.

In some embodiments, the first probe comprises between about 20 and about 50 nucleotides.

In some embodiments, the second probe comprises between about 20 and about 50 nucleotides.

In some embodiments, the first probe comprises biotin.

In some embodiments, the bead is magnetic.

In some embodiments, the method further comprises concentrating the markers adjacent or in proximity to the array of nanopores with a magnetic field.

In another aspect, the disclosure provides a method for sequencing, counting, and/or sorting molecules, comprising: (a) providing an array of nanopores, wherein an individual nanopore of said array is individually addressable by an adjacent sensing electrode operated in non-faradic mode or faradaic mode; (b) providing a plurality of magnetically attractable beads each coupled to a molecule among a plurality of molecules to be sequenced, counted and/or sorted using the array of nanopores; concentrating the magnetically attractable beads in the vicinity of the array of nanopores with a magnet; and (c) sequencing, counting and/or sorting the molecules with the array of nanopores.

In some embodiments, the magnetically attractable beads comprise metal.

In some embodiments, the magnetically attractable beads comprise a permanent magnetic material.

In some embodiments, the concentration of the magnetically attractable beads prior to concentrating the magnetically attractable beads is at most 100 femto-molar.

In some embodiments, the concentration of the magnetically attractable beads prior to concentrating the magnetically attractable beads is at most 10 femto-molar.

In some embodiments, the concentration of the magnetically attractable beads near the array of nanopores is increased by at least 100-fold by said concentrating.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "FIG." and "Figure" herein), of which:

DETAILED DESCRIPTION

Figure 1:
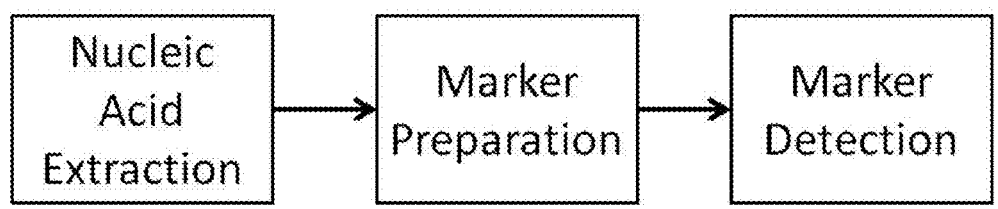
FIG. 1 schematically shows the steps of the method.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "nanopore," as used herein, generally refers to a pore, channel or passage formed or otherwise provided in a membrane. A membrane may be an organic membrane, such as a lipid bilayer, or a synthetic membrane, such as a membrane formed of a polymeric material. The membrane may be a polymeric material. The nanopore may be disposed adjacent or in proximity to a sensing circuit or an electrode coupled to a sensing circuit, such as, for example, a complementary metal-oxide semiconductor (CMOS) or field effect transistor (FET) circuit. In some examples, a nanopore has a characteristic width or diameter on the order of 0.1 nanometers (nm) to about 1000 nm. Some nanopores are proteins. Alpha hemolysis is an example of a protein nanopore.

The term "nucleic acid," as used herein, generally refers to a molecule comprising one or more nucleic acid subunits. A nucleic acid may include one or more subunits selected from adenosine (A), cytosine (C), guanine (G), thymine (T) and uracil (U), or variants thereof. A nucleotide can include A, C, G, T or U, or variants thereof. A nucleotide can include any subunit that can be incorporated into a growing nucleic acid strand. Such subunit can be an A, C, G, T, or U, or any other subunit that is specific to one or more complementary A, C, G, T or U, or complementary to a purine (i.e., A or G, or variant thereof) or a pyrimidine (i.e., C, T or U, or variant thereof). A subunit can enable individual nucleic acid bases or groups of bases (e.g., AA, TA, AT, GC, CG, CT, TC, GT, TG, AC, CA, or uracil-counterparts thereof) to be resolved. In some examples, a nucleic acid is deoxyribonucleic acid (DNA) or ribonucleic acid (RNA), or derivatives thereof. A nucleic acid may be single-stranded or double stranded.

The term "polymerase," as used herein, generally refers to any enzyme capable of catalyzing a polymerization reaction. Examples of polymerases include, without limitation, a nucleic acid polymerase or a ligase. A polymerase can be a polymerization enzyme.

Methods and Devices

In an aspect, the disclosure provides methods and devices for molecular counting and/or sorting comprises providing an array of nanopores, where each nanopore is individually addressable and disposed adjacent to a sensing electrode. Individually addressable nanopores can each provide their own electronic signal (e.g., using the sensing electrodes). In some cases, the voltage applied to each individually addressable nanopore can be individually controlled. In some cases, the nanopores are divided into groups, where various groups of nanopores are individually addressable (e.g., provide a signal and/or can have individually applied voltages) with respect to each other.

The method can comprise providing a plurality of marker entities (also "markers" herein) capable of being captured and identified by the nanopores. The marker entities can be any molecule or molecular complex capable of being captured and identified by the nanopores. The disclosure provides some examples of marker entities and molecular entities.

In some cases, the method comprises capturing and identifying the marker entities with the array of nanopores. The sensing electrodes can be operated in a non-faradaic (or capacitive) sensing mode (e.g., where the electrode and electrolyte do not perform a redox reaction). In some embodiments, the marker entities are captured and identified quickly (e.g., at a rate of at least about 1 marker entity per second per nanopore).

FIG. 1 shows an example of the steps of the method. In some cases, the markers are generated from a nucleic acid sample. The nucleic acid sample can be extracted from an organism, tissue or cell. The marker entities can be prepared according to the methods described herein (see, e.g., FIG. 8 and the corresponding text). The marker entities can be detected with the aid of a nanopore array.

The devices and methods of the present disclosure can be capable of detecting and/or counting several different marker entities (e.g., on the same nanopore and/or in parallel on different portions of the nanopore array). The method can be capable of counting and/or sorting any suitable number of marker entities. In some cases, the method is capable of counting and/or sorting about 2, about 3, about 4, about 5, about 6, about 7, about 8, about 10, about 12, about 15, about 20, about 25, about 30, or about 50 different types of marker entities. In some cases, the method is capable of counting and/or sorting at least about 2, at least about 3, at least about 4, at least about 5, at least about 6, at least about 7, at least about 8, at least about 10, at least about 12, at least about 15, at least about 20, at least about 25, at least about 30, or at least about 50 different types of marker entities.

Nanopore Arrays

Provided herein are systems and methods for counting, binning and sorting with the aid of a nanopore. The nanopore may be formed or otherwise embedded in a membrane disposed adjacent to a sensing electrode of a sensing circuit, such as an integrated circuit. The integrated circuit may be an application specific integrated circuit (ASIC). In some examples, the integrated circuit is a field effect transistor or a complementary metal-oxide semiconductor (CMOS). The sensing circuit may be situated in a chip or other device having the nanopore, or off of the chip or device, such as in an off-chip configuration. The semiconductor can be any semiconductor, including, without limitation, Group IV (e.g., silicon) and Group III-V semiconductors (e.g., gallium arsenide).

In some cases, as a marker entity flows through or adjacent to the nanopore, the sensing circuit detects an electrical signal associated with the marker entity. The marker entity may be a subunit of a larger molecule. The marker entity may be a byproduct of a nucleotide incorporation event or other interaction between a tagged nucleic acid and the nanopore or a species adjacent to the nanopore, such as an enzyme that cleaves a marker entity from a nucleic acid. The marker entity may remain attached to a nucleic acid. A detected signal may be collected and stored in a memory location, and later used to count the marker entities. The collected signal may be processed to account for any abnormalities in the detected signal, such as errors.

Figure 2A:
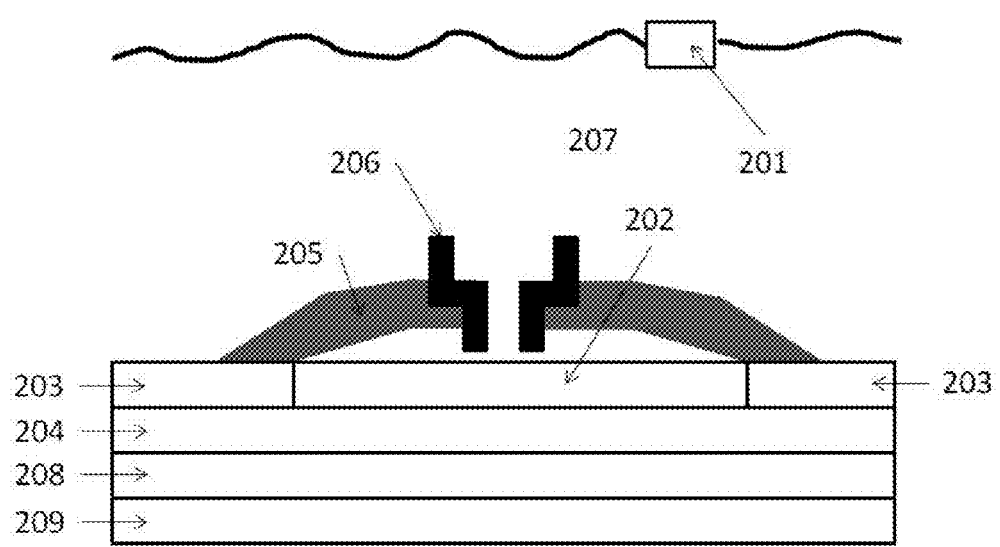
FIGS. 2A, 2B and 2C show examples of nanopore detectors, where FIG. 2A has the nanopore disposed upon the electrode, FIG. 2B has the nanopore inserted in a membrane over a well and FIG. 2C has the nanopore over a protruding electrode.

FIG. 2 shows an examples of a nanopore detector (or sensor) having temperature control, as may be prepared according to methods described in U.S. Patent Application Publication No. 2011/0193570, which is entirely incorporated herein by reference. With reference to FIG. 2A, the nanopore detector comprises a top electrode 201 in contact with a conductive solution (e.g., salt solution) 207. A bottom conductive electrode 202 is near, adjacent, or in proximity to a nanopore 206, which is inserted in a membrane 205. In some instances, the bottom conductive electrode 202 is embedded in a semiconductor 203 in which is embedded electrical circuitry in a semiconductor substrate 204. A surface of the semiconductor 203 may be treated to be hydrophobic. A sample having marker entities being detected goes through the pore in the nanopore 206. The semiconductor chip sensor is placed in package 208 and this, in turn, is in the vicinity of a temperature control element 209. The temperature control element 209 may be a thermoelectric heating and/or cooling device (e.g., Peltier device). Multiple nanopore detectors may form a nanopore array.

Figure 2B:
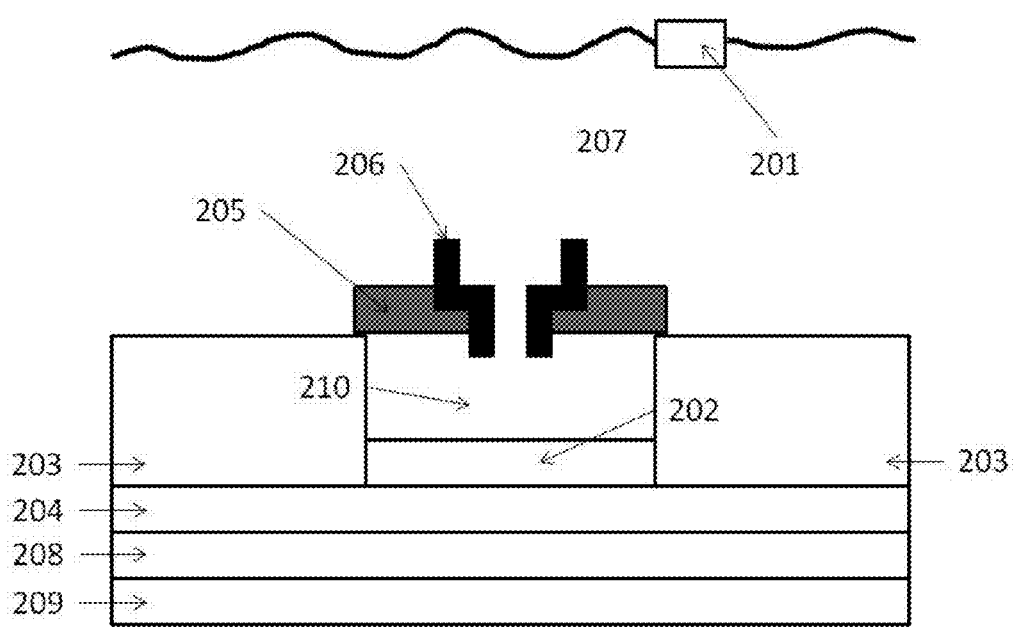
Figure 2C:
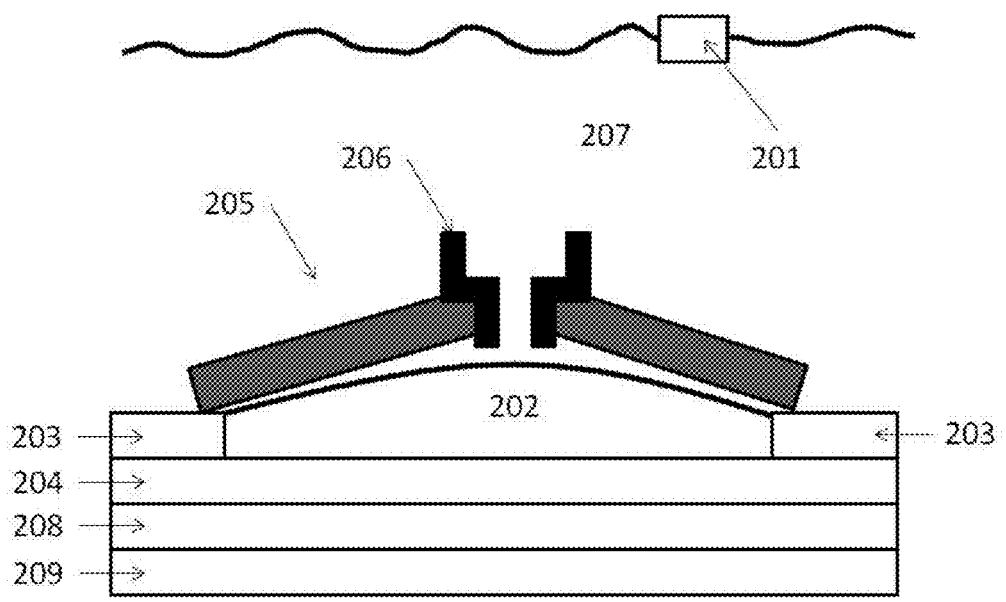

With reference to FIG. 2B, where like numerals represent like elements, the membrane 205 can be disposed over a well 210, where the sensor 202 forms part of the surface of the well. FIG. 2C shows an example in which the electrode 202 protrudes from the treated semiconductor surface 203.

In some examples, the membrane 205 forms on the bottom conductive electrode 202 and not on the semiconductor 203. The membrane 205 in such a case may form coupling interactions with the bottom conductive electrode 202. In some cases, however, the membrane 205 forms on the bottom conductive electrode 202 and the semiconductor 203. As an alternative, the membrane 205 can form on the semiconductor 203 and not on the bottom conductive electrode 202, but may extend over the bottom conductive electrode 202.

Nanopores may be used to count, sort or bin marker entities indirectly, in some cases with electrical detection. Indirect detection may be any method where a marker entity does not pass through the nanopore. The marker entity may pass within any suitable distance from and/or proximity to the nanopore, in some cases within a distance such that marker entities are detected in the nanopore.

Byproducts of nucleotide incorporation events may be detected by the nanopore. "Nucleotide incorporation events" are the incorporation of a nucleotide into a growing polynucleotide chain. A byproduct may be correlated with the incorporation of a given type nucleotide. The nucleotide incorporation events are generally catalyzed by an enzyme, such as DNA polymerase, and use base pair interactions with a template molecule to choose amongst the available nucleotides for incorporation at each location. In some cases, the marker entities are used to sequence a nucleic acid molecule.

Figure 3:
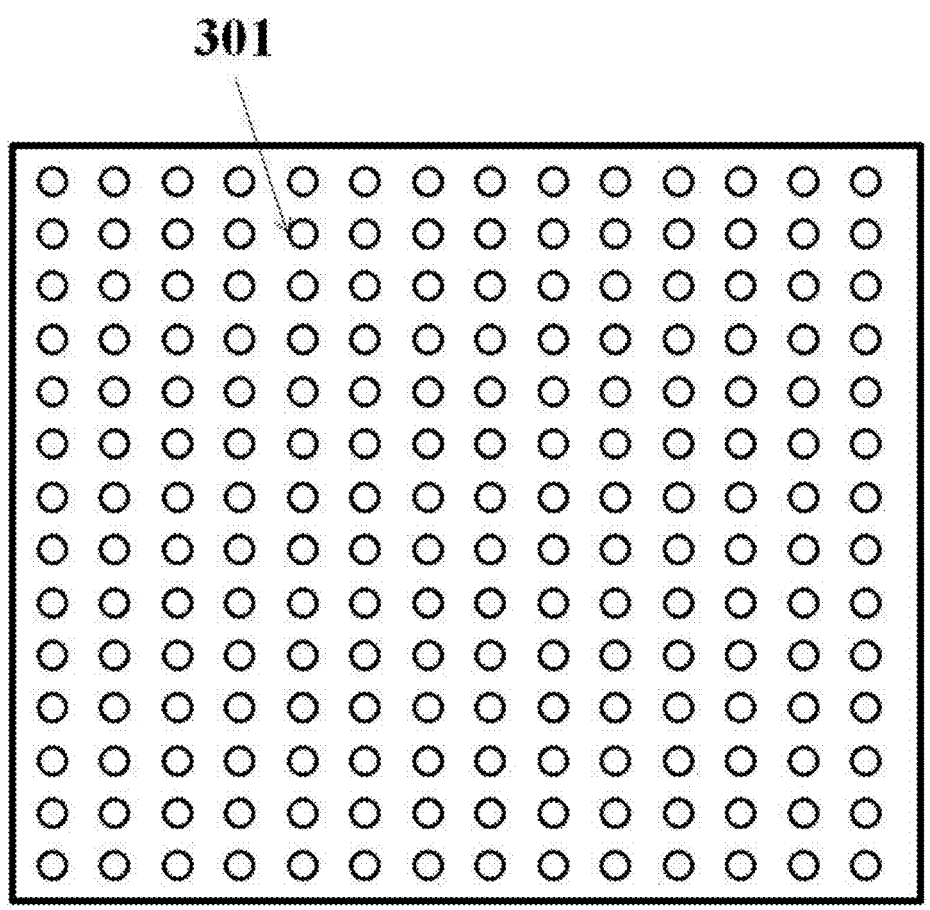
FIG. 3 shows an array of nanopore detectors.

The nanopores can form an array. The disclosure provides an array of nanopore detectors (or sensors) for detecting marker entities. With reference to FIG. 3, a plurality of marker entities may be detected on an array of nanopore detectors. Here, each nanopore location (e.g., 301) comprises a nanopore, in some cases attached to a polymerase enzyme and/or phosphatase enzymes. There is also generally a sensor at each array location as described elsewhere herein. Each of the nanopores can be individually addressable.

The array of nanopores may have any suitable number of nanopores. In some instances, the array comprises about 200, about 400, about 600, about 800, about 1000, about 1500, about 2000, about 3000, about 4000, about 5000, about 10000, about 15000, about 20000, about 40000, about 60000, about 80000, about 100000, about 200000, about 400000, about 600000, about 800000, about 1000000, and the like nanopores. The array can comprise at least 200, at least 400, at least 600, at least 800, at least 1000, at least 1500, at least 2000, at least 3000, at least 4000, at least 5000, at least 10000, at least 15000, at least 20000, at least 40000, at least 60000, at least 80000, at least 100000, at least 200000, at least 400000, at least 600000, at least 800000, or at least 1000000 nanopores.

In some cases, a marker entity is presented or concentrated near a nanopore (e.g., magnetically). A nanopore sensor adjacent to a nanopore may detect an individual marker entity, or a plurality of marker entities. One or more signals associated with marker entities may be detected and processed to yield an averaged signal.

Marker entities may be detected by the sensor as a function of time. Marker entities detected with time may be used to determine the identity of the marker entity, such as with the aid of a computer system (see, e.g., FIG. 13) that is programmed to record sensor data and generate the count, sorting or binning functions from the data.

The array of nanopore detectors may have a high density of discrete sites. For example, a relatively large number of sites per unit area (i.e., density) allows for the construction of smaller devices, which are portable, low-cost, or have other advantageous features. An individual site in the array can be an individually addressable site. A large number of sites comprising a nanopore and a sensing circuit may allow for a relatively large number of marker entities to be detected at once. Such a system may increase the throughput and/or decrease the cost of counting, sorting or binning A marker entity may be detected using a sensor (or detector) having a substrate with a surface comprising discrete sites, each individual site having a nanopore, and in some cases a polymerase attached to the nanopore and a sensing circuit adjacent to the nanopore. The system may further comprise a flow cell in fluid communication with the substrate, the flow cell adapted to deliver one or more reagents to the substrate.

The surface comprises any suitable density of discrete sites (e.g., a density suitable for determining marker entities in a given amount of time or for a given cost). Each discrete site can include a sensor. The surface may have a density of discrete sites greater than or equal to about 500 sites per 1 $mm^2$. In some embodiments, the surface has a density of discrete sites of about 200, about 300, about 400, about 500, about 600, about 700, about 800, about 900, about 1000, about 2000, about 3000, about 4000, about 5000, about 6000, about 7000, about 8000, about 9000, about 10000, about 20000, about 40000, about 60000, about 80000, about 100000, or about 500000 sites per 1 $mm^2$. In some cases, the surface has a density of discrete sites of at least 200, at least 300, at least 400, at least 500, at least 600, at least 700, at least 800, at least 900, at least 1000, at least 2000, at least 3000, at least 4000, at least 5000, at least 6000, at least 7000, at least 8000, at least 9000, at least 10000, at least 20000, at least 40000, at least 60000, at least 80000, at least 100000, or at least 500000 sites per 1 $mm^2$.

In some cases, the array of nanopores is configured to have a plurality of regions (e.g., lanes) capable of performing the method on different samples. The samples can be different, or the sample can be divided into separate volumes with different assays performed on each volume.

Figure 4:
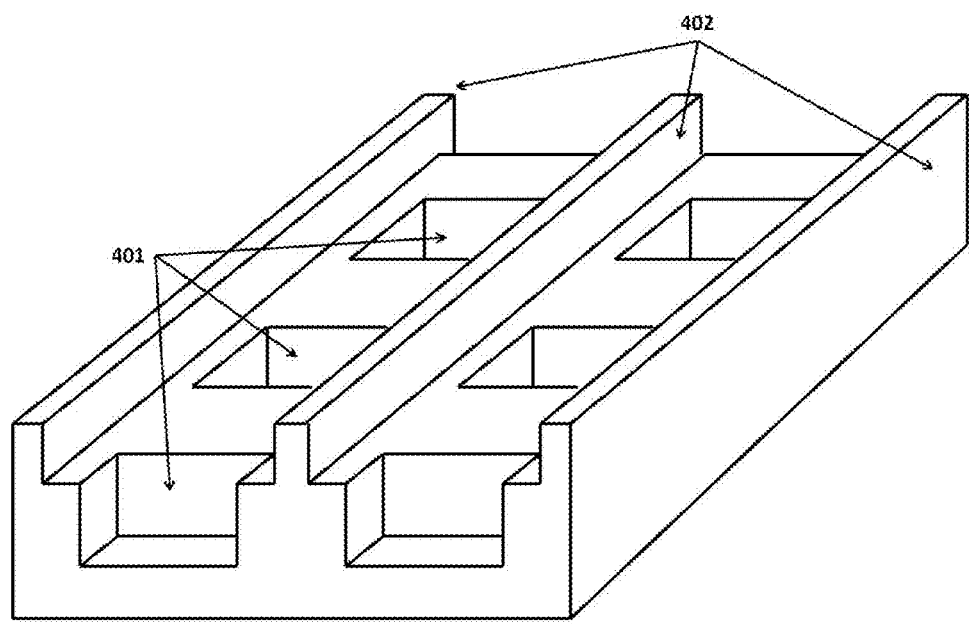
FIG. 4 shows the array of nanopores divided into two lanes.

In some cases, a plurality of wells (including any subset of the total number of wells) comprises a common electrolyte pool. Each well can have a membrane with a nanopore disposed over it and a sensing electrode below or in the well. As shown in FIG. 4, the wells 401 may be separated into rows by walls 402 such that the row of wells shares a common electrolyte pool above the wells. Separating the biochip into sections as described here can allow multiple samples to be analyzed on a single biochip (e.g., by putting different samples in different sections of the chip).

Sensing Electrodes and Operation Thereof

Figure 5:
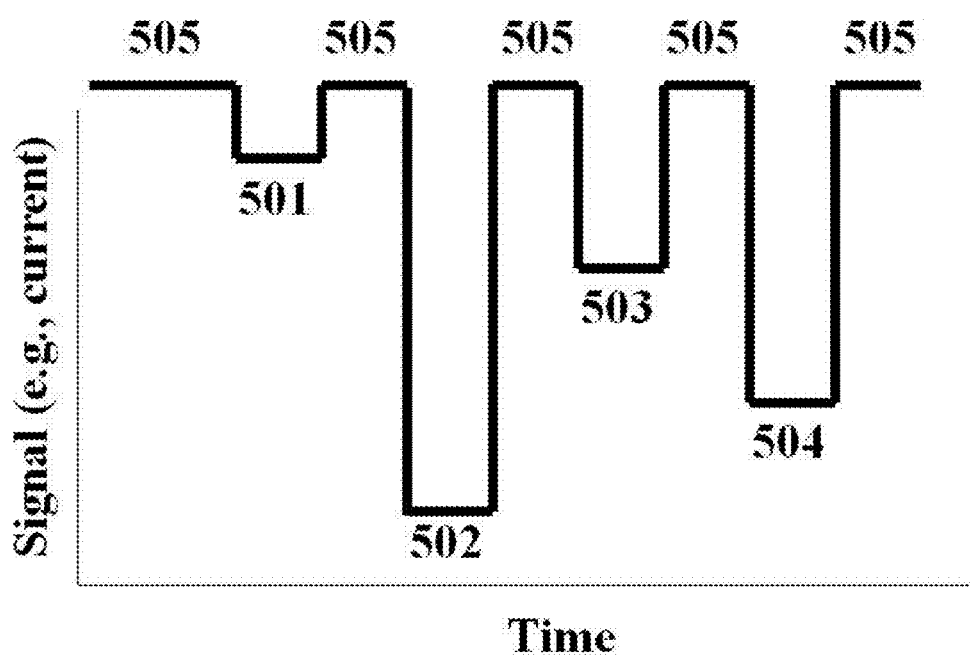
FIG. 5 shows an example of a signal generated by marker entities (or markers) passing into a nanopore.

The marker entities can be identified based on a current that flows through the nanopore and/or a voltage at which the marker entity leaves (or is removed from) of the nanopore (e.g., fall out voltage). FIG. 5 shows a prophetic plot where marker entities block the current flowing through the nanopore over time. The current is at a baseline level 505 in the absence of a marker entity in the nanopore. The current can be reduced to different extents when different tags are located in the nanopore (e.g., 501, 502, 503, 504). Detection of marker entities based on the fall out voltage is described below.

The current can be detected with a sensing electrode (e.g., which can include or be in electrical communication with a sensing circuit). The sensing electrodes can be capable of either Faradaic or non-Faradaic sensing modes.

In Fardaic conduction mode, metal electrodes and a conductive salt can react (e.g., perform an oxidation/reduction (redox) reaction) to form a new metal species and an electron that is later sensed by the chip's sensor circuit. In Faradaic mode, a flow of ions can be generated by an applied electrical potential between the electrodes, which can cause the electrodes to react with ions in solution. In an example of silver chloride (AgCl) electrodes, an excess electron at one electrode under an applied potential can cause chloride anion (Cl$^-$) to be expelled while a lack of electrons at the other electrode can cause the silver (Ag) present to react with Cl$^-$ and form AgCl. This system (e.g., reduction: electron+AgCl à Ag(s)+Cl$^-$; oxidation: Cl$^-$+Ag(s) à AgCl+ electron) is described as Faradaic and can be representative of any model using the oxidation and reduction of any metal to produce a flow of ions. To maintain a balance of Ag and AgCl at the electrodes and to help balance ions present on either side of a bilayer or membrane and nanopore as the system is operated, it may be necessary to occasionally (or frequently) reverse the potential on the electrodes to reverse the reaction.

The flow of ions can also be generated by non-Faradaic means. In non-Faradaic mode (also "capacitive mode" and "fast mode" herein), the metal electrode and the salt do not generally react (e.g., and do not perform a redox reaction). The result can be that the metal electrode does not generally form a new species. In non-Faradaic mode, a flow of salt ions can be established by applying a voltage (or electrical potential) drop across a capacitive double layer existing between a metal and a salt or liquid. Under a potential, the capacitance of the double layer can be substantial enough such that the double layer can conduct and hold charge until the double layer (capacitor) reaches its maximum ability to store charge. Removing the potential and letting the capacitor discharge through the nanopore can produce a flow of salt ions that can be detected by the sensor circuit. By switching the voltage fast enough (e.g., switching the polarity or magnitude of the voltage), a series of discharge cycles can be strung together that are close enough in time to detect and represent the effects of molecules interacting with the nanopore. This technique has the benefit of allowing a very small metal or non-metal conducting electrode to produce ion and current flow without the electrode being degraded or changing over the course of the experiment.

Capacitive methods can be used to attract and repel ions to and from the electrodes, but the ions may not cause a chemical reaction at the surface of the electrodes. Electron flow can still be induced at the electrodes; however it can be the result of charge influence, not physical chemical reactions and electron ejection or capture. The manipulation of charge and ionic flow in the non-Faradaic method also can benefit from occasionally (or frequently) reversing the potential applied to the electrodes; for example to reset a capacitance value to zero or substantially zero, or an undetectable limit.

Methods of the present disclosure can be implemented with Faradic metal electrode nanopore arrays, however the non-Faradaic operation can result in significantly faster counting and run for significantly longer periods of time. In addition, the non-Faradaic approach can be the basis for very fast attraction and capture of a marker entity. It can also then be used to repulse and or expulse a marker entity near or in the vicinity of a nanopore barrel.

In both Faradaic and non-Faradaic modes, the act of reversing the potential can cause the marker entity in the nanopore to reverse direction. In nanopore systems, it can be difficult to take readings of both positive and negative currents. In the case of reading only positive currents, all negative applied potential readings can be read as zero. As a result, the position of the marker entity can be lost. In some instances, the marker entity may even be ejected from the nanopore and it can be necessary to re-capture the marker entity during the next positive applied potential.

Use of Faradaic or non-Faradaic electrical detection of marker entities using electrodes of small or microscopic size (e.g., as is the case in a massively parallel nanopore array) can cause the marker entities to reverse direction. Molecules can be detected and polymers sequenced (marker entities can comprise polymers) in such a system by measuring the flow of ions past a molecule being held or passing through a nanopore. To create many pores and make parallel readings of many similar or different molecules, many electrodes and their associated nanopores can be used. To create many electrodes/nanopores in a small area, the electrodes may be small. Small electrodes and/or the small amount of reagents in the side of electrodes sealed with a membrane or bilayer material can cause electrodes to lose their effectiveness in translating ionic flow to electrical current.

Figure 6:
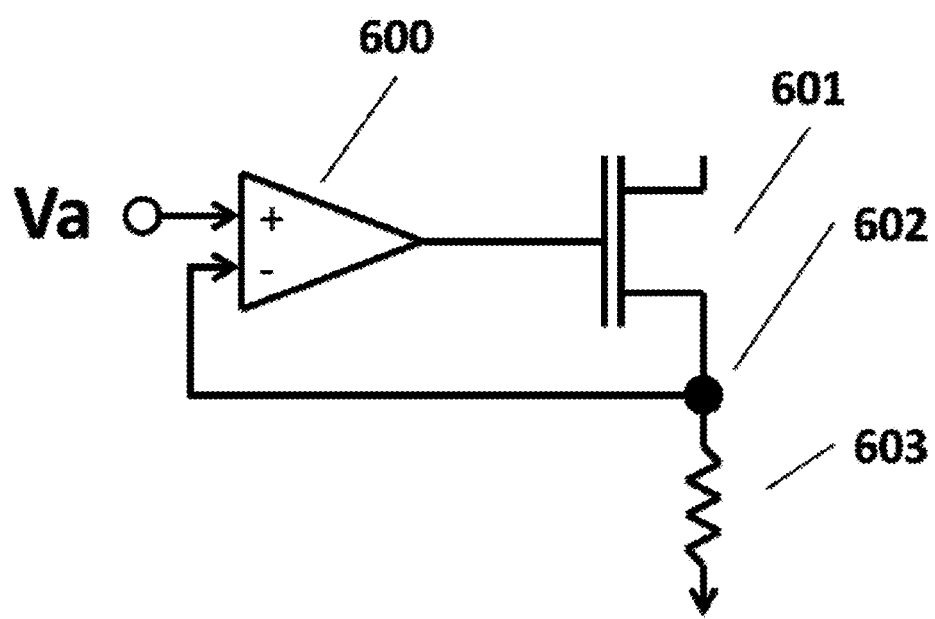
FIG. 6 shows an example of a compact sensor circuit.

FIG. 6 shows an example of a compact sensing circuit. An applied voltage Va can be applied to an opamp 600 ahead of a MOSFET current conveyor gate 601. Also shown here are an electrode 602 and the resistance of the marker entity detected by the device 603.

An applied voltage Va can drive the current conveyor gate 601. The resulting voltage on the electrode is then Va-Vt where Vt is the threshold voltage of the MOSFET. In some instances, this results in limited control of the actual voltage applied to the electrode as a MOSFET threshold voltage can vary considerably over process, voltage, temperature, and even between devices within a chip. This Vt variation can be greater at low current levels where sub-threshold leakage effects can come into play. Therefore, in order to provide better control of the applied voltage, an opamp can be used in a follower feedback configuration with the current conveyor device. This can ensure that the voltage applied to the electrode is Va, independent of variation of the MOSFET threshold voltage. In some cases, the voltage applied to the electrode is calibrated using the fall-out voltage as described below.

The sensors and/or methods described herein can be operated in non-faradaic mode or in faradic mode. In some cases, including trehalose in the solution(s) allows faradic mode electrodes to operate for about an hour, which can be long enough to perform molecular counting and/or sorting as described herein. In some cases, faradic readings may give better resolution than non-faradaic operation.

Marker Entities and Detection Thereof

Figure 7:
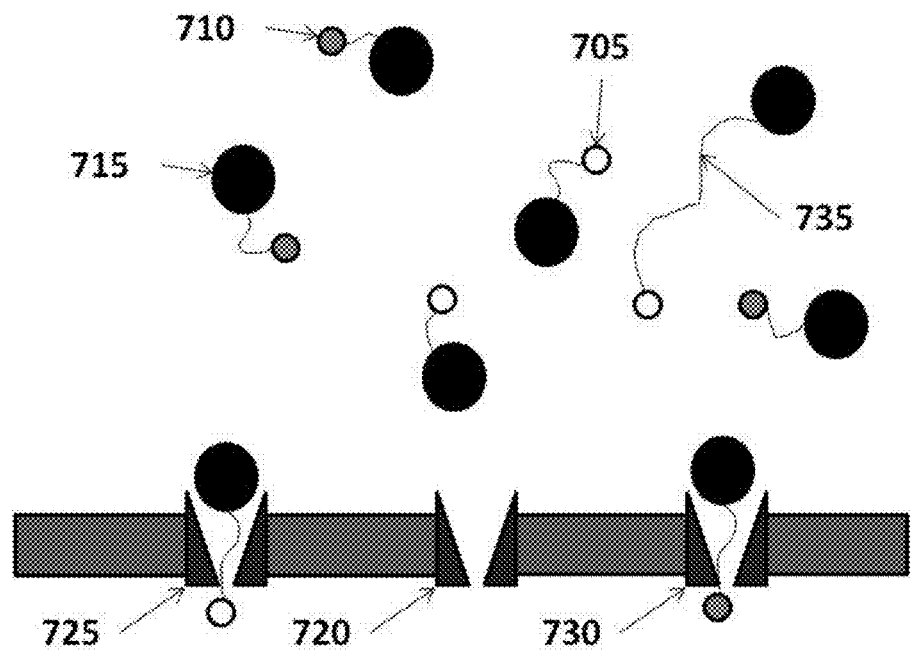
FIG. 7 shows an example of using nanopores to count, sort or bin marker entities.

Methods of the present disclosure can include capturing and identifying the marker entities with the array of nanopores. The marker entities can be any molecule or molecular complex, but in some cases they are polymers (e.g., nucleic acids or peptides) attached to beads. FIG. 7 shows an example of marker entities having different polymers (in this case two different markers 705 and 710) attached to beads 715. The polymer portion of the marker entities can be drawn into the nanopore where they block the current flowing through the nanopore. Each different type of marker entity can provide a unique electronic signature, where a nanopore having no marker entity 720 is distinguished from a nanopore having a first marker entity 725, which is distinguished from a nanopore having a second marker entity 730.

The plurality of marker entities can comprise any number of different marker entities and/or the methods and devices described herein can be capable of distinguishing between any number of different marker entities. In some cases, the marker entities have different polymers attached to a bead (e.g., 705 vs. 710). Examples of different polymers include poly-ethylene glycol (PEG), nucleic acids having different sequences, or peptides having different sequences. In some cases, the marker entities have the same polymers (e.g., both PEG) attached to a bead, but the length of the polymer is varied (e.g., 705 vs. 735). In some cases, the type of polymer can be identified based on a level of current (e.g., FIG. 5) and the length of the polymer can be identified based on its fall-out voltage (e.g., FIG. 10).

The sample can have any number of different marker entities. In some cases, the sample has about 2, about 3, about 4, about 5, about 6, about 7, about 8, about 10, about 12, about 15, about 20, about 25, about 30, or about 50 different types of marker entities. In some cases, the sample has at least about 2, at least about 3, at least about 4, at least about 5, at least about 6, at least about 7, at least about 8, at least about 10, at least about 12, at least about 15, at least about 20, at least about 25, at least about 30, or at least about 50 different types of marker entities.

The plurality of marker entities can comprise (polymer) tails having any number of different lengths. In some cases, the molecular entities comprise tails having about 2, about 3, about 4, about 5, about 6, about 7, about 8, about 9, or about 10 different lengths. In some cases, the molecular entities comprise tails having at least about 2, at least about 3, at least about 4, at least about 5, at least about 6, at least about 7, at least about 8, at least about 9, or at least about 10 different lengths.

In some cases, the marker entities comprise a single stranded nucleic acid molecule attached to a bead. The marker entities can be generated in any suitable way.

Figure 8:
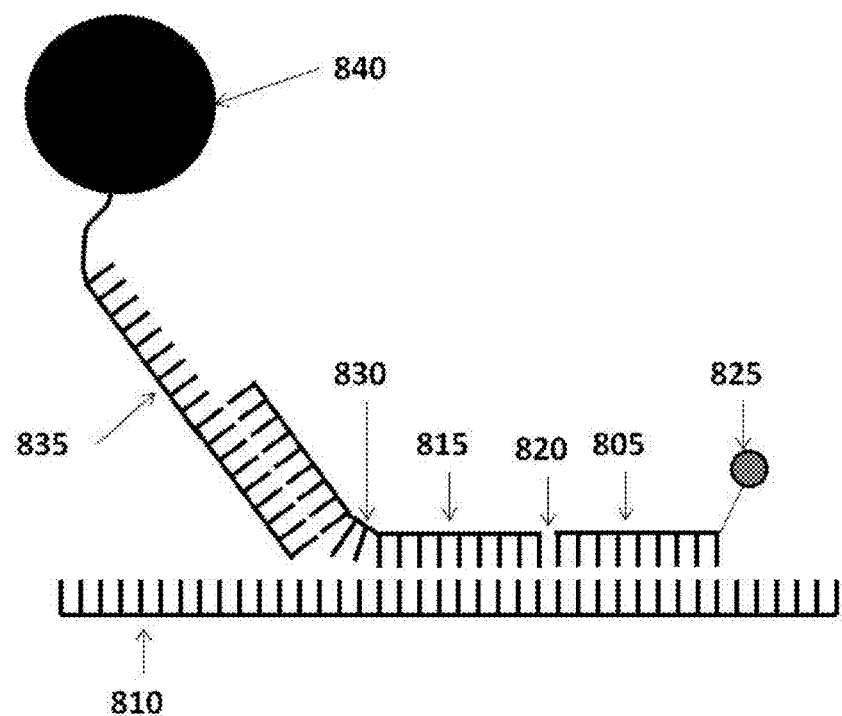
FIG. 8 shows an example of a marker entity and method for generation of a marker entity.

With reference to FIG. 8, in some cases, the marker entities are generated by hybridizing a first probe 805 to a genomic DNA sample 810, hybridizing a second probe 815 to the genomic DNA sample adjacent to the first probe, and ligating 820 the first probe to the second probe to produce a combined probe. In some cases, the first probe has a biotin molecule attached 825. The second probe can have a sequence of bases 830 (e.g., two bases) that provide a unique current level in the nanopore for a given marker. In some cases, the second probe can determine the current level, and by varying the length of the first probe, the length of the marker entity's tail can be varied to provide a second means of determining the identity of the marker entity (e.g., current level and tail length via fall-out voltage). The second probe can hybridize to an oligonucleotide 835 that is attached to a bead 840 (e.g., for capture and isolation of the combined probe). The method can comprise capturing the combined probe with a bead attached to an oligonucleotide, wherein the oligonucleotide hybridizes with the combined probe.

The marker entities, first probes, second probes and/or combined probes can have any suitable length. In some cases, the marker entities, first probes, second probes and/or combined probes comprise nucleotides. In some instances, the first probe comprises about 10, about 15, about 20, about 25, about 30, about 35, about 40, about 45, about 50, about 60, about 80, or about 100 nucleotides. In some instances, the first probe comprises at least about 10, at least about 15, at least about 20, at least about 25, at least about 30, at least about 35, at least about 40, at least about 45, at least about 50, at least about 60, at least about 80, or at least about 100 nucleotides. In some embodiments, the first probe comprises at most about 10, at most about 15, at most about 20, at most about 25, at most about 30, at most about 35, at most about 40, at most about 45, at most about 50, at most about 60, at most about 80, or at most about 100 nucleotides. In some cases, the first probe comprises between about 20 and about 50 nucleotides.

In some instances, the second probe comprises about 10, about 15, about 20, about 25, about 30, about 35, about 40, about 45, about 50, about 60, about 80, or about 100 nucleotides. In some instances, the second probe comprises at least about 10, at least about 15, at least about 20, at least about 25, at least about 30, at least about 35, at least about 40, at least about 45, at least about 50, at least about 60, at least about 80, or at least about 100 nucleotides. In some embodiments, the second probe comprises at most about 10, at most about 15, at most about 20, at most about 25, at most about 30, at most about 35, at most about 40, at most about 45, at most about 50, at most about 60, at most about 80, or at most about 100 nucleotides. In some cases, the second probe comprises between about 20 and about 50 nucleotides.

Since the first and second probes hybridize next to each other at a particular site on sample DNA, the marker entities carry information derived from the sample DNA. A slight temperature increase can dissociate the combined probe from the sample. In some cases, this cycle is repeated until a region of interest of the DNA sample has multiple combined probes (e.g., the sample can generate multiple marker entities and/or a marker entity can be formed from more than two probes).

For linear sequencing or for detection in a nanopore these individual combined probes can have incorporated select molecules that allow the isolation of and subsequent linking of each of the combined probes into long read strands (e.g., containing from 2 up to 10,000 or more combined probes). These combined probes in these read strands can be from one specific sequence region from one sample, resulting a read strand of repeated identical combined probes. In some cases, these read strands can be from multiple specific sequence regions from one sample resulting in a read strand containing a mixture of different (from 2 to 1,000 or more) combined probes. One way to link these combined probes is to label the 5' end of one and the 3' end of the other. The labels can be any combination of F4B and HiNyc (i.e., Solulink), streptavidin and biotin, or an alkyne and azide (i.e., click chemistry).

In some cases, strand mediated ligation can be used to ligate the individual hybridized and ligated probes together into a single long strand for single-loading and sequencing in a nanopore based system. Such a system may include ligation and separation of un-ligated probes and sample DNA from the desired ligated probes.

In addition, these read strands can be from multiple specific sequence regions from multiple different samples resulting in read strands containing a mix of different (from 2 to 1,000s or more) combined probes with each probe having a sample identifier or sample bar-code incorporated.

Each combined probe can have any combination or number of features such as; unique hybridization sections of probe molecules that bind adjacent to each other at a specific site selected for enrichment; non-binding section that identifies what sample number the full probe is from; and biotin or other attachment molecule(s) that allows separation of desired ligated probes from un-ligated probes.

In some embodiments of the method, a modification of the polymer can be made to allow the molecule to thread through the nanopore and yet be unable to reverse direction through the nanopore. This probe method can use the incorporation of uni-directional gate sections (e.g., to allow non-enzymatic, strand sequencing of the product of this reaction on massively parallel electrical detection, nanopore based systems).

Figure 9:
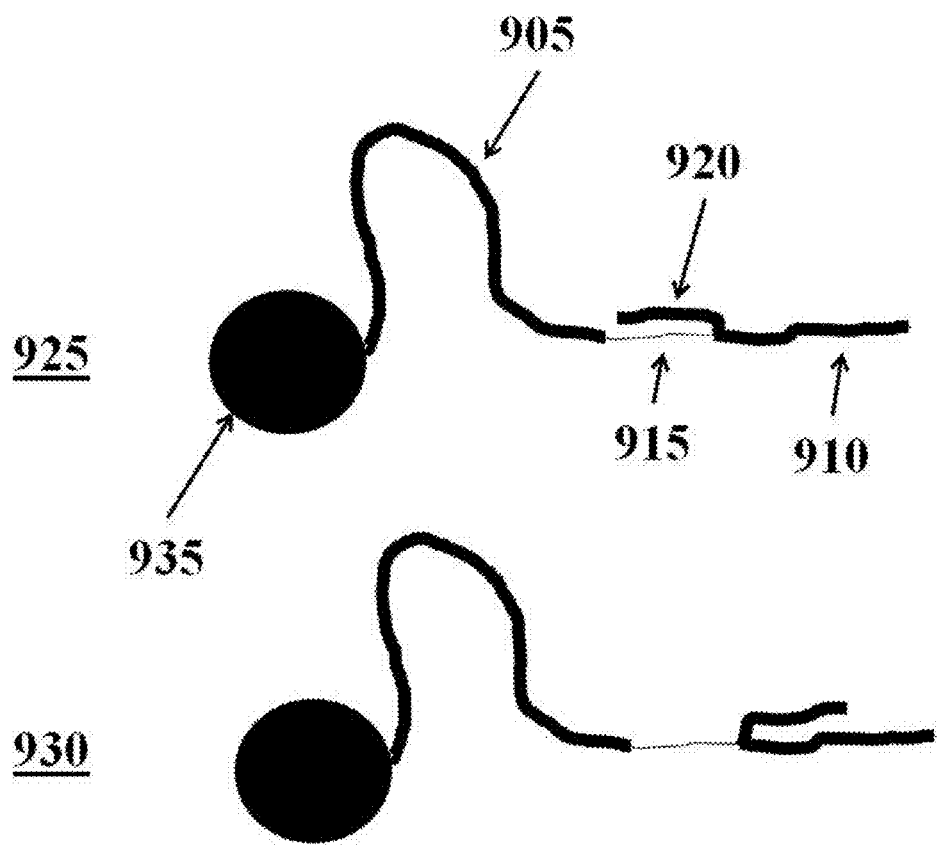
FIG. 9 shows an example of a marker entity having a uni-directional gate.

In some cases, the marker entity is only capable of passing through the nanopore in one direction (e.g., without reversing direction). The marker entity can have a hinged gate attached to the marker entity that is thin enough to pass through the nanopore when the gate is aligned with the marker entity tail in one direction, but not in another direction. With reference to FIG. 9, the disclosure provides a marker entity molecule, comprising a first polymer chain 905 comprising a first segment 910 and a second segment 915, where the second segment is narrower than the first segment. The second segment can have a width that is smaller than the narrowest opening of the nanopore. The marker entity molecule can include a second polymer chain 920 comprising two ends, where a first end is affixed to the first polymer chain adjacent to the second segment and a second end is not affixed to the first polymer chain. The marker entity molecule is capable of being threaded through a nanopore in a first direction where the second polymer chain aligns adjacent to the second segment 925. In some cases, the marker entity molecule is not capable of being threaded through the nanopore in a second direction where the second polymer chain does not align adjacent to the second segment 930. The second direction can be opposite the first direction.

The first and/or second polymer chains can comprise nucleotides. In some cases, the second polymer chain base pairs with the first polymer chain when the second polymer chain does not align adjacent to the second segment. In some instances, the first polymer chain is affixed to a bead 935.

The second segment can comprise any polymer or other molecule that is thin enough to pass through a nanopore when aligned with the gate (second polymer). For instance, the second segment can comprise a-basic nucleotides (i.e., a nucleic acid chain not having any nucleic acid bases) or a carbon chain.

The creation of the gate can be done in many ways. The molecule may be synthesized directly or the molecule can be appended or ligated together. For example, a DNA strand can be created with and alkyne labeled nucleotide incorporated wherever a gate is to be attached. A second azide end-labeled nucleotide (e.g., that may be antisense to the nucleotide latch area) can be attached using click chemistry. Other attachment chemistries and techniques maybe utilized including commercial methods (e.g., Solulink) or Amine-COOH combination.

Fall Out Voltage

Figure 10:
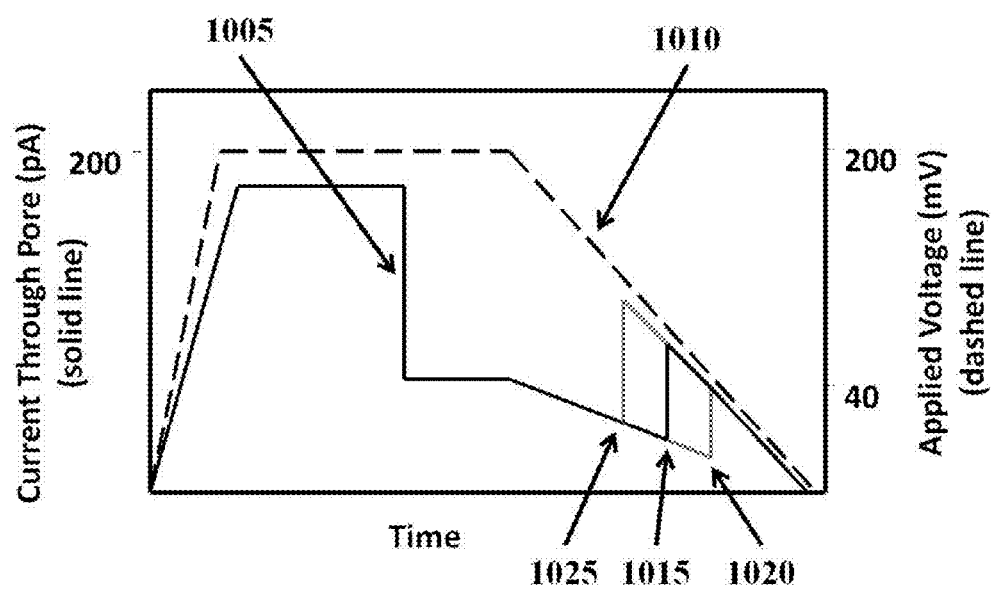
FIG. 10 shows an example of the identification of a marker entity based on its fall-out voltage.

The marker entities can be identified based on a voltage at which the marker entities are dislodged from or leave (or removed from) the nanopore (fall-out voltage). In non-Faradaic mode, marker entities having tails (e.g., polymers) of various lengths can fall out of the nanopore at different voltages as the voltage decreases. FIG. 10 shows a plot of current through the nanopore (solid lines) and applied voltage (dashed lines) versus time. The current can decrease when a molecule is captured in the nanopore 1005. As the applied voltage is decreased over time 1010, the current decreases until the molecule falls out of the nanopore, at which time the current increases to the expected level at the applied voltage. The applied voltage at which the molecule falls out can depend on the length of the molecule. For example, a marker entity having a 30 base tail can fall out around 40 milli-volts (mV) 1015, while a marker entity having a 50 base tail can fall out around 10 mV 1020. As shown in this example, marker entities having tails shorter than 30 bases can fall out of the nanopore at applied voltages higher than 40 mV 1025.

Various current levels and fall-out voltages can be used to identify marker entities. For example, the ability to detect 4 different current levels and 2 different fall-out voltages can allow the use of 8 different marker entities.

In some cases, the applied voltage can be calibrated or re-calibrated using the fall-out voltage. The calibration can permit the identification of the marker entities. In some examples, calibration includes programming a computer processor of or associated with a biochip (or nanopore sensor apparatus) with known marker entities having identifiable signals, and storing the signals in a memory location of or associated with the biochip for subsequent measurements.

Figure 11:
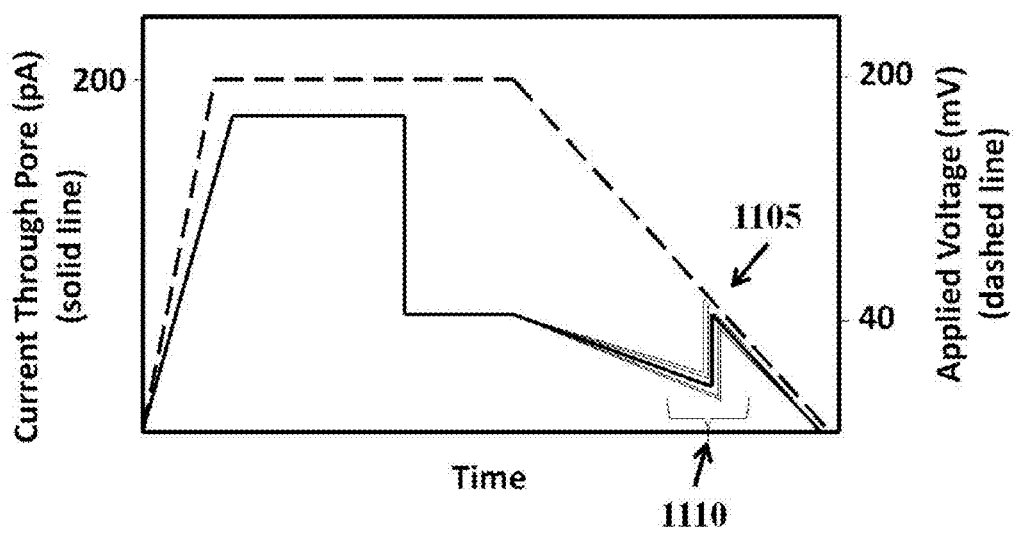
FIG. 11 shows an example of using the fall-out voltage to calibrate the applied voltage.

Referring to FIG. 11, for a given marker entity having an average fall-out voltage 1105, there can be variation 1110 in the fall-out voltage for different nanopores or for different measurements on the same nanopore over time. Adjusting this fall-out voltage to an expected value can make the data easier to interpret and/or more accurate.

Molecule-specific output signals from single-molecule nanopore sensor devices can originate from the presence of an electrochemical potential difference across an ionically impermeable membrane surrounded by an electrolyte solution. This trans-membrane potential difference can determine the strength of the nanopore-specific electrochemical current that can be detected by electronics within the device via either sacrificial (i.e., Faradaic) or nonsacrificial (i.e., non-Faradaic) reactions occurring at the electrode surfaces.

For any given state of the nanopore (i.e., open channel, captured state, etc.), the time-dependent trans-membrane potential can act as an input signal that can determine the resulting current flowing through the nanopore complex as a function of time. This nanopore current can provide the specific molecular signal output by the nanopore sensor device. The open-channel nanopore current can be modulated to varying degrees by the interactions between the nanopore and the captured molecules which partially block the flow of ions through the channel.

These modulations can exhibit specificity for the type of molecule that has been captured, allowing some molecules to be identified directly from their nanopore current modulations. For a given molecule type and a fixed set of device conditions, the degree of modulation of the open-channel nanopore current by a captured molecule of this type can vary depending on the trans-membrane potential applied, mapping each type of molecule to a particular current-vs.-voltage (I-V) curve.

Systematically variable offsets between the applied voltage settings and the trans-membrane potential can introduce horizontal shifts of this I-V curve along the horizontal voltage axis, potentially reducing the accuracy of molecular identification based on the measured current signals reported by the nanopore sensor device as an output signal. Therefore, uncontrolled offset between the applied and trans-membrane potentials can be problematic for accurately comparing measurements of the same molecule under the same conditions.

This so-called "potential offset" between the externally-applied potential and the actual trans-membrane potential can vary both within and between experiments. Variations in potential offset can be caused by both variations in initial conditions and by time-dependent variations (drift) in the electrochemical conditions within the nanopore sensor device.

Removing these measurement errors can be done as described here by calibrating the time-dependent offset between the applied voltage and the trans-membrane potential for each experiment. Physically, the probability of observing escape events of nanopore-captured molecules can depend on the trans-membrane potential applied and this probability distribution can be the same for identical samples of molecules under the same conditions (e.g., the sample may be a mixture of different types of molecules provided that their proportions do not vary between samples). In some cases, the distribution of voltages where escape events occur for a fixed sample type provides a measure of the offset between the applied and trans-membrane potentials. This information can be used in order to calibrate the applied voltage across the nanopore, eliminating systematic sources of error caused by potential offsets within and between experiments and improving the accuracy of molecular identification and other measurements.

For a given nanopore sensor apparatus operated with the same molecular sample and reagents, the expected value of the distribution of escape voltages can be estimated from a statistical sample of the single molecular escape events (although each individual event can be a stochastic process subject to random fluctuations). This estimate can be time-dependent to account for temporal drift of the potential offset within the experiment. This can correct for the variable difference between applied voltage settings and actual voltage felt at the pore, effectively "lining up" all the measurements horizontally when plotted in I-V space.

In some cases, potential (i.e. voltage) offset calibration does not account for current gain and current offset variations, which can also be calibrated for improved accuracy and reproducibility of nanopore current measurements. However, potential offset calibration is generally done prior to gain and offset correction to prevent errors in estimating the current gain and current offset variations, since these in turn can involve fitting current vs. voltage (I-V) curves, and the results of these fits are affected by variations in voltage offset (i.e., shifting the data left-to-right (horizontally) in I-V space can introduce errors in current gain and current offset calibration).

In some cases, the applied voltage is calibrated. The calibrating can include estimating an expected escape voltage distribution versus time for the sensing electrode. The calibration can then compute a difference between the expected escape voltage distribution and a reference point (e.g., an arbitrary reference point, such as zero). The calibration can then shift the applied voltage by the computed difference. In some cases, the applied voltage decreases over time.

In some cases, a distribution of expected escape voltages versus time is estimated. In some instances, the reference point is zero volts. The method can removes detected variations in expected escape voltage distribution. In some cases, the method is performed on a plurality of independently addressable nanopores each adjacent to a sensing electrode.

In some embodiments, the presence of the marker entity in the nanopore reduces the current measured with the sensing electrode at the applied voltage.

In some instances, the calibration increases the accuracy of the method when compared to performing the method without calibration. In some cases, the calibration compensates for changes in electrochemical conditions over time. In some instances, the calibration compensates for different nanopores having different electrochemical conditions in a device having a plurality of nanopores. In some embodiments, the calibration compensates for different electrochemical conditions for each performance of the method. In some cases, the method further comprises calibrating variations in a current gain and/or variations in a current offset.

Fast, Precise and Accurate Counting

Provided herein are methods and devices for identifying and/or counting marker entities using nanopores. In some cases, the identifying and/or counting is fast, precise and/or accurate.

The marker entities can be identified and/or counted at any suitable rate. In some cases, the marker entities are identified and/or counted at a rate of about 0.2, about 0.5, about 1, about 2, about 3, about 4, about 5, about 6, about 7, about 8, about 9, about 10, about 15, about 20, or about 30 marker entities per second per nanopore. In some cases, the marker entities are identified and/or counted at a rate of at least about 0.2, at least about 0.5, at least about 1, at least about 2, at least about 3, at least about 4, at least about 5, at least about 6, at least about 7, at least about 8, at least about 9, at least about 10, at least about 15, at least about 20, or at least about 30 marker entities per second per nanopore.

In some instances, the method and/or nanopore array is capable of identifying about 500,000, about 1 million, about 5 million, about 10 million, about 50 million, about 100 million, about 500 million, or about 1 billion marker entities per hour. In some cases, the method and/or nanopore array is capable of identifying at least about 500,000, at least about 1 million, at least about 5 million, at least about 10 million, at least about 50 million, at least about 100 million, at least about 500 million, or at least about 1 billion marker entities per hour.

The methods and devices described herein can be used to determine copy number variation or relative RNA expression levels. In some cases, the methods are very precise (e.g., can detect very small differences in copy number variation or relative RNA expression levels). In some instances, the method is capable of detecting differences in copy number of about 0.01%, about 0.05%, about 0.1%, about 0.5%, about 1%, about 2%, about 3%, or about 5%. In some instances, the method is capable of detecting differences in copy number of less than about 0.01%, less than about 0.05%, less than about 0.1%, less than about 0.5%, less than about 1%, less than about 2%, less than about 3%, or less than about 5%.

The methods and devices described herein can be used to perform an alternative to an enzyme-linked immunosorbent assay (ELISA) (e.g., quantify dilute or rare entities). In some cases, the device or method is capable of quantifying marker entities that comprise about 0.01%, about 0.05%, about 0.1%, about 0.5%, about 1%, about 2%, about 3%, or about 5% of the total number of marker entities. In some instances, the device or method is capable of quantifying marker entities that comprise less than about 0.01%, less than about 0.05%, less than about 0.1%, less than about 0.5%, less than about 1%, less than about 2%, less than about 3%, or less than about 5% of the total number of marker entities.

Sorting and Binning

The present disclosure provides devices and methods that can be used to sort the marker entities. In some cases, the sorted marker entities are collected. The marker entities can be collected in separate reservoirs according to their identity (e.g., binned).

Figure 12:
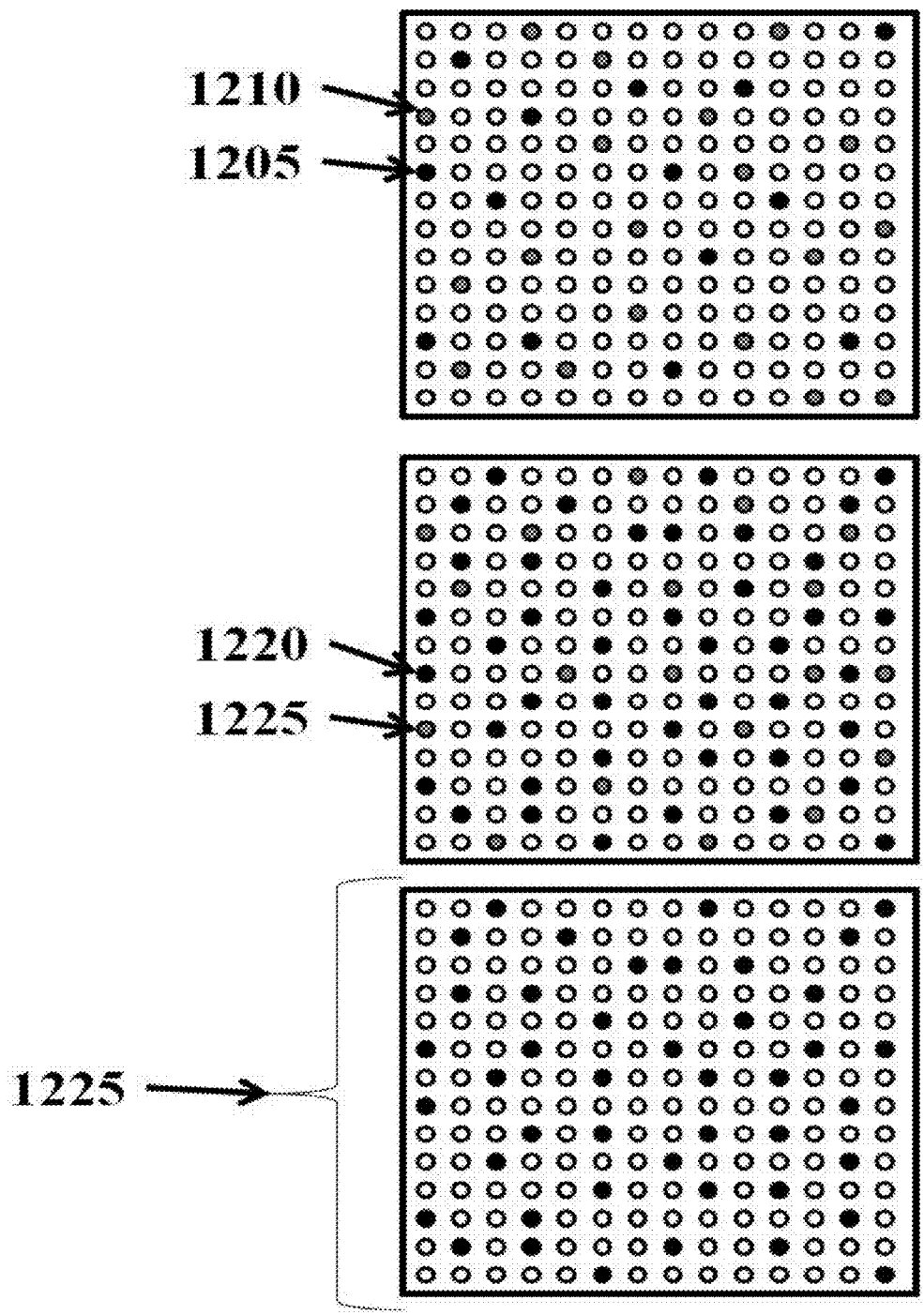
FIG. 12 shows an example of a device and/or method for sorting and binning molecular entities.

FIG. 12 shows an example of a device and/or method for sorting and binning molecular entities. Nanopores not having a molecular entity are depicted as open circles. Nanopores having a molecular entity to be sorted and binned are depicted as circles filled with black. Nanopores having a molecular entity other than the one to be sorted and binned are depicted as circles filled with gray. The nanopores of the nanopore array can capture and identify marker entities including ones to be sorted 1205 and ones other than to be sorted 1210. In some cases, the molecular entities to be sorted are retained in the nanopore (e.g., by maintaining a suitably high applied voltage). The molecular entities that are other than the ones to be sorted can be expelled from the nanopore (e.g., by switching off or reversing the polarity of the applied voltage), in some cases while still retaining the molecular entities to be sorted (e.g., because the nanopores are individually addressable). The nanopores that do not have a captured marker entity to be sorted can continue to capture, identify, and either retain or expel marker entities based on their identity. During this continued process, additional marker entities to be sorted can be captured 1220. After any suitable time and/or number of marker entities to be sorted have been captured and identified, most or all of the marker entities other than those to be sorted can be expelled 1225 to result in a nanopore array having all (or mostly all) marker entities to be sorted. At this point, most or all of the marker entities to be sorted can be expelled (e.g., as a group) from the nanopore array. In some cases, the expelled marker entities to be sorted can be binned (e.g., as a group). In some cases, the method can be repeated to specifically capture a second group of marker entities to be sorted (e.g., other than the first group of marker entities to be sorted). In some cases, a first group of nanopores of the nanopore array capture and retain a first group of marker entities to be sorted and a second group of nanopores of the nanopore array capture and retain a second group of marker entities to be sorted.

In some cases, the marker entities to be sorted are released as a group when the percentage of marker entities to be sorted that are captured is suitably high. In some instances, the marker entities to be sorted are released when about 50%, about 60%, about 70%, about 80%, about 90%, about 95%, about 99%, about 99.5%, or about 99.9% of the marker entities to be sorted are captured. In some cases, the marker entities to be sorted are released when at least about 50%, at least about 60%, at least about 70%, at least about 80%, at least about 90%, at least about 95%, at least about 99%, at least about 99.5%, or at least about 99.9% of the marker entities to be sorted are captured.

In some cases, the marker entities to be sorted are released as a group when the ratio of marker entities to be sorted divided by marker entities other than the marker entities to be sorted that are captured and identified by the nanopores decreases below a threshold. In some cases, the threshold is about 10%, about 5%, about 3%, about 1%, about 0.5%, about 0.1%, about 0.05%, or about 0.01%. In some instances, the threshold is less than about 10%, less than about 5%, less than about 3%, less than about 1%, less than about 0.5%, less than about 0.1%, less than about 0.05%, or less than about 0.01%.

Magnetic Concentration

In some cases, the marker entities are at a low concentration in a bulk solution in contact with the nanopore array (e.g., below a concentration at which the rate of capture by the nanopores is suitably high), but are concentrated near the nanopores using magnetism (e.g., such that the rate of capture and identification of the marker entities is suitably high). In some cases, the bead portion of the marker entities (e.g., 935 of FIG. 9) is magnetic or paramagnetic. In some cases, the method comprises concentrating the marker entities near the array of nanopores with a magnetic field, which can be provided by a magnet (e.g., a permanent magnet or an electromagnet).

In an aspect, a method for sequencing, counting, and/or sorting molecules comprises providing an array of nanopores, where each nanopore is individually addressable and disposed adjacent to a sensing electrode. The method can also comprise providing a plurality of magnetically attractable (or active) beads coupled to a molecule to be sequenced, counted and/or sorted using the array of nanopores and concentrating the magnetically attractable beads in the vicinity of the array of nanopores with a magnet. The method can further comprise sequencing, counting and/or sorting the molecules with the array of nanopores.

In some cases, the magnetically attractable beads comprise metal. In some instances, the magnetically attractable beads comprise a permanent magnetic material.

The marker entities and/or magnetically attractable beads can be at any suitably low initial concentration (e.g., in a bulk solution in contact with the nanopore array) prior to concentrating the marker entities and/or magnetically attractable beads. In some cases, the initial concentration is about 1 femto-molar (fM), about 5 fM, about 10 fM, about 50 fM, about 100 fM, about 500 fM, or about 1 micro-molar (μM). In some cases, the initial concentration is at most about 1 femto-molar (fM), at most about 5 fM, at most about 10 fM, at most about 50 fM, at most about 100 fM, at most about 500 fM, or at most about 1 micro-molar (μM).

The marker entities and/or magnetically attractable beads can be concentrated near the nanopores to any suitable extent (e.g., a suitably high ratio of the concentration near the nanopores after concentration to the initial concentration in the bulk solution). In some cases, the concentration of the magnetically attractable beads near the array of nanopores is increased by about 5-fold, about 10-fold, about 50-fold, about 100-fold, about 500-fold, about 1000-fold, about 5000-fold, or about 10000-fold. In some embodiments, the concentration of the magnetically attractable beads near the array of nanopores is increased by at least about 5-fold, at least about 10-fold, at least about 50-fold, at least about 100-fold, at least about 500-fold, at least about 1000-fold, at least about 5000-fold, or at least about 10000-fold.

Computer Systems

The devices described herein can be coupled to a computer system (e.g., that collects data from and/or controls each of the individually addressable nanopores). In some cases, the methods described herein are performed with the aid of a computer system. The computer system can include one or more computer processors and a memory location coupled to the computer processor. The memory location comprises machine-executable code that, upon execution by the computer processor, implements any of the methods described herein.

Figure 13:
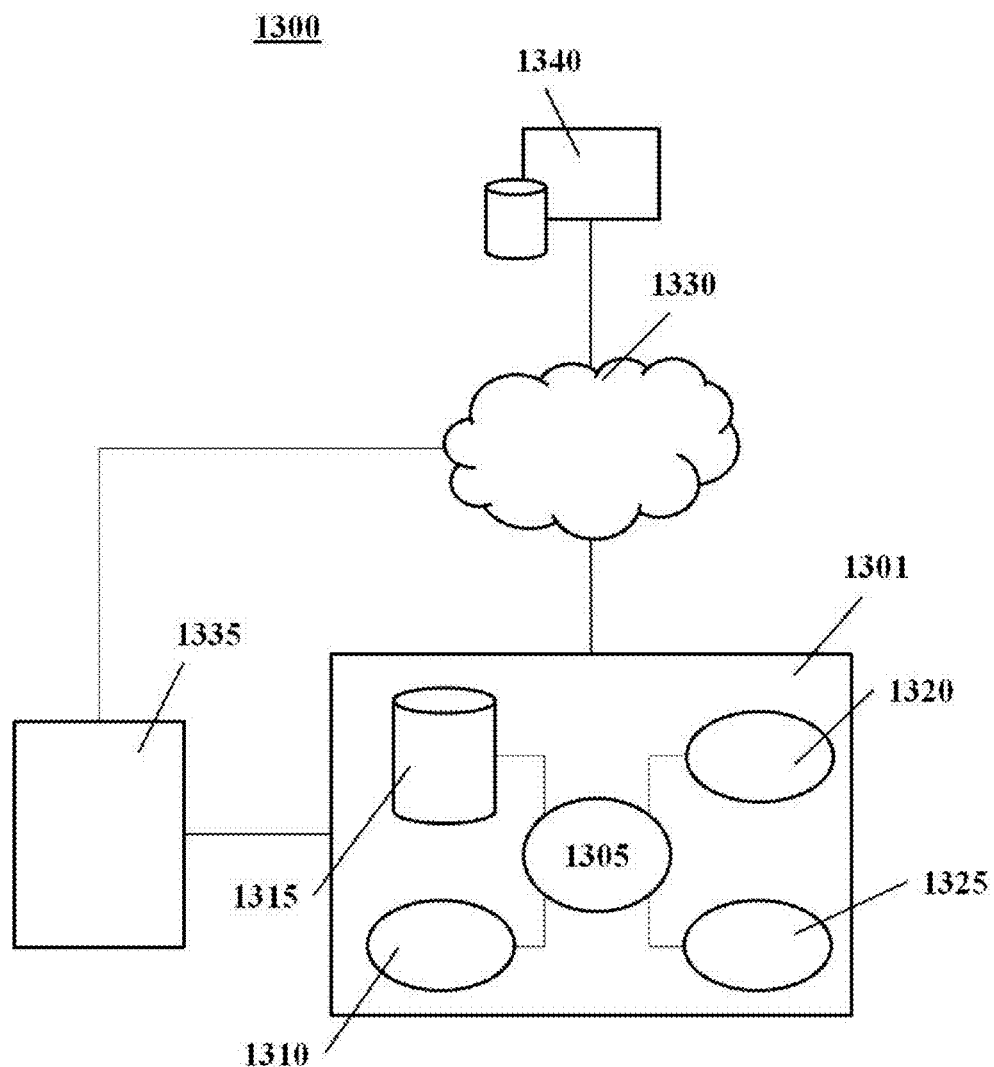
FIG. 13 shows an example of a computer system that is programmed or otherwise configured to implement methods of the present disclosure.

FIG. 13 shows a system 1300 programmed or otherwise configured to control or regulate one or more process parameters of a system of the present disclosure. The system 1300 includes a computer server ("server") 1301 that is programmed to implement methods disclosed herein. The server 1301 includes a central processing unit (CPU, also "processor" and "computer processor" herein) 1305, which can be a single core or multi core processor, or a plurality of processors for parallel processing. The server 1301 also includes memory 1310 (e.g., random-access memory, read-only memory, flash memory), electronic storage unit 1315 (e.g., hard disk), communication interface 1320 (e.g., network adapter) for communicating with one or more other systems, and peripheral devices 1325, such as cache, other memory, data storage and/or electronic display adapters. The memory 1310, storage unit 1315, interface 1320 and peripheral devices 1325 are in communication with the CPU 1305 through a communication bus (solid lines), such as a motherboard. The storage unit 1315 can be a data storage unit (or data repository) for storing data. The server 1301 can be operatively coupled to a computer network ("network") 1330 with the aid of the communication interface 1320. The network 1330 can be the Internet, an internet and/or extranet, or an intranet and/or extranet that is in communication with the Internet. The network 1330 in some cases is a telecommunication and/or data network. The network 1330 can include one or more computer servers, which can enable distributed computing, such as cloud computing. The network 1330, in some cases with the aid of the server 1301, can implement a peer-to-peer network, which may enable devices coupled to the server 1301 to behave as a client or a server. The server 1301 can be coupled to a system 1335 either directly or through the network 1330. The system 1335 can be configured to perform nucleic acid (e.g., DNA, RNA) or polymeric (e.g., protein) sequencing or molecular counting.

The storage unit 1315 can store process parameters (e.g., calibration parameters) of the system 1335. The process parameters can include charging and discharging parameters. The server 1301 in some cases can include one or more additional data storage units that are external to the server 1301, such as located on a remote server that is in communication with the server 1301 through an intranet or the Internet.

The server 1301 can communicate with one or more remote computer systems through the network 1330. In the illustrated example, the server 1301 is in communication with a remote computer system 1340. The remote computer system 1340 can be, for example, a personal computers (e.g., portable PC), slate or tablet PC (e.g., Apple® iPad, Samsung® Galaxy Tab), telephone, Smart phone (e.g., Apple® iPhone, Android-enabled device, Blackberry®), or personal digital assistant.

In some situations, the system 1300 includes a single server 1301. In other situations, the system 1300 includes multiple servers in communication with one another through an intranet and/or the Internet.

Methods as described herein can be implemented by way of machine (or computer processor) executable code (or software) stored on an electronic storage location of the server 1301, such as, for example, on the memory 1310 or electronic storage unit 1315. During use, the code can be executed by the processor 1305. In some cases, the code can be retrieved from the storage unit 1315 and stored on the memory 1310 for ready access by the processor 1305. In some situations, the electronic storage unit 1315 can be precluded, and machine-executable instructions are stored on memory 1310. Alternatively, the code can be executed on the second computer system 1340.

The code can be pre-compiled and configured for use with a machine have a processor adapted to execute the code, or can be compiled during runtime. The code can be supplied in a programming language that can be selected to enable the code to execute in a pre-compiled or as-compiled fashion.

Aspects of the systems and methods provided herein, such as the server 1301, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

Various parameters of the system described herein can be presented to a user on a user interface (UI) of an electronic device of the user. Examples of UI's include, without limitation, a graphical user interface (GUI) and web-based user interface. The UI (e.g., GUI) can be provided on a display of an electronic device of the user or server 1301. The display can be a capacitive or resistive touch display. Such displays can be used with other systems and methods of the disclosure.

The following examples are intended to illustrate, but not limit, the invention.

EXAMPLES

Example 1: Creation of a Non-Faradaic Array and Demonstration of Marker Detection A nanopore sensor chip is created with electrode metal optimized for non-Faradaic, fast mode (e.g., non-Faradaic) operation. The electrode processing results in an individual electrode with a capacitance of 20 femto-Farads (fF) to 60 fF. A non-Faradaic conducting salt solution is tested and selected to provide a repeatable and appropriate open channel current level. The salt solution enables voltages sufficient to readily capture free floating marker entities. The hardware and software of the nanopore sensor chip is modified for fast mode operation. Continuous operation of the nanopore sensor chip is demonstrated with a minimum of 5 active pores for 30 minutes. The pores capture (e.g., DNA) markers at a rate of at least 2 per second. Markers are tested and 4 different markers are selected that give 4 different current levels with 95% or greater accuracy over 1,800 marker captures. The test is replicated 5 times.

Example 2: Optimization and Characterization of the Chip

Operating nanopores are created that are capable of operating in fast mode. A minimum of forty pores are created in five out of ten consecutive attempts. Pores are created that are capable of operating in fast mode and have a minimum of twenty pores that last for a minimum of thirty minutes. The chip is operated in fast mode and demonstrates the counting of marker entities. A solution containing two different markers is read with at least twenty pores operating in fast mode. Markers are read at a rate of two markers per second across twenty pores for thirty minutes for a total of 72,000 reads. The anticipated read ratios are checked with the expected ratios. The fallout voltage for four different markers is characterized to determine if marker length can be used to increase the potential pool of markers.

Example 3: Fast Molecular Sensing

A nanopore array having 264 individually addressable nanopores is provided. About 75 of the nanopores are operating for the purpose of sequencing. A mixture of four different marker entities is provided. An operating nanopore captures and identifies the marker entities at a rate of about four marker entities per second. The nanopore array reads about 300 marker entities per chip per second, about 18,000 marker entities per chip per minute, or about 1,080,000 marker entities per chip per hour. In two hours, the nanopore array reads about 2,160,000 marker entities per chip.

Example 4: Fast Molecular Sensing

A nanopore array having 264 individually addressable nanopores is provided. About seventy five of the nanopores are operating. A mixture of eight different marker entities is provided with some of the markers having different tail lengths. The nanopore captures and identifies the marker entities at a rate of about one per second per operating nanopore. The nanopore array reads about seventy five marker entities per chip per second. The nanopore array reads about 4,500 marker entities per chip per minute, about 270,000 marker entities per chip per hour, or about 540,000 marker entities per chip in two hours.

Example 5: Fast Molecular Sensing

A nanopore array having 132,000 individually addressable nanopores is provided. About 50,000 of the nanopores are operating. A mixture of four different marker entities is provided. The nanopore captures and identifies the marker entities at a rate of about four per second per operating nanopore. The nanopore array reads about 200,000 marker entities per chip per second, about 12,000,000 marker entities per chip per minute, or about 720,000,000 marker entities per chip in one hour.

Example 6: Fast Molecular Sensing

A nanopore array having 132,000 individually addressable nanopores is provided. About 50,000 of the nanopores are operating. A mixture of eight different marker entities is provided with some of the markers having different tail lengths. The nanopore captures and identifies the marker entities at a rate of about one per second per operating nanopore. The nanopore array reads about 50,000 marker entities per chip per second, about 3,000,000 marker entities per chip per minute, or about 180,000,000 marker entities per chip in one hour.

Example 7: Fast Molecular Sensing

A nanopore array having 132,000 individually addressable nanopores is provided. The array is divided into four lanes each having about 20,000 nanopores. Each lane has about 7,500 operating nanopores and is capable of performing a different assay. A mixture of thirty two different marker entities is provided. The mixture is divided amongst the four lanes. The nanopore captures and identifies the marker entities at a rate of about four per second per operating nanopore. The nanopore array reads about 30,000 marker entities per lane per second, about 18,000,000 marker entities per lane per minute, or about 108,000,000 marker entities per lane in one hour.

Example 8: Fast Molecular Sensing

A 96 well plate is populated with beads such that each well has beads that capture one marker. The markers that are created from one sample have unique binding sites that allow them to bind to a specific bead. The mix of markers can be configured so that for each bead, eight different markers can bind. The remaining markers have binding sites for other beads. The entire marker mix is created so that only 8 markers are allowed for each different bead. In this example, there are 8 markers for each bead and 96 beads for 768 unique markers separated into groups of 8 per well.

The sample solution is sequentially exposed to each well, drawing the magnetic beads to the bottom of the well after each exposure and moving the sample solution to the next well for exposure. A collection of markers can be separated for detection using the nanopore detection technique described here. Other methods of spatially separating the beads to allow for the separate collection markers can be performed (e.g., beads serially exposed to one solution containing markers, or beads spatially positioned at known locations on a nanopore array chip).

The collection of markers in each well of the 96 well plate can be melted off the bead or left on the bead and flowed through a channel on the nanopore detector chip. The marker can be flushed from the flow cell after detection in the flow cell and the next different collection of markers attached to a different bead can be loaded and detected or counted. The complete flushing of beads and markers can be assisted by the magnetic properties of the beads. Applying a magnetic attraction force as well as liquid washing force can help insure the complete rinsing of nearly all markers from a flow cell.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for molecular counting and/or sorting, comprising:
   a. providing a nanopore array comprising multiple nanopores in a lipid bilayer membrane and multiple nanopore detectors, each of said nanopore detectors comprising a top electrode and a bottom conductive electrode, wherein the top electrode is in contact with a conductive solution and the bottom conductive electrode is positioned adjacent to an individual nanopore, wherein the bottom conductive electrode is adapted to detect a current passing through the individual nanopore, and wherein the individual nanopore is individually addressable by the adjacent bottom conductive electrode;
   b. providing a plurality of oligonucleotide markers wherein each of the oligonucleotide markers comprise oligonucleotides of between 10 and 100 nucleotides, wherein at least two of the oligonucleotides of between 10 and 100 nucleotides hybridize with a nucleic acid sample to produce a combined probe, wherein a first oligonucleotide of the at least two of the oligonucleotides has a label molecule attached to it and a second oligonucleotide has a sequence of bases that provides a unique current level in the nanopore for each of the oligonucleotide markers, wherein the second oligonucleotide hybridizes to an oligonucleotide that is attached to a bead for capture and isolation of the combined probe,
   c. capturing and identifying at least one oligonucleotide marker within the plurality of oligonucleotide markers with at least one nanopore and at least one nanopore detector within the nanopore array at a rate of at least about one oligonucleotide marker per second per at least one nanopore, wherein the at least one oligonucleotide marker is identified based on a current that flows through the individual nanopore and an applied voltage of between 40 to 200 mV at which the oligonucleotide marker is released from the nanopore, and
   d. sorting the plurality of oligonucleotide markers into selected oligonucleotide markers and unselected oligonucleotide markers, wherein the selected oligonucleotide markers are captured, identified, and held in nanopores within the nanopore array, and wherein the unselected oligonucleotide markers are captured, identified, and released from nanopores within the nanopore array; and further wherein the selected oligonucleotide markers are released as a group when the percentage of selected oligonucleotide markers that are captured is at least 50%.

2. The method of claim 1, wherein the nanopore array is configured to have a plurality of regions configured to perform the method on different samples.

3. The method of claim 1, wherein each oligonucleotide marker within the plurality of oligonucleotide markers are generated by:
   a. hybridizing the first oligonucleotide to a first region of the nucleic acid sample;
   b. hybridizing the second oligonucleotide to a second region of the nucleic acid sample, wherein the first region of the nucleic acid sample is adjacent to the second region of the nucleic acid sample, thereby positioning the second oligonucleotide adjacent to the first oligonucleotide;
   c. ligating the first oligonucleotide to the second oligonucleotide to produce the combined probe; and
   d. hybridizing the second oligonucleotide to the oligonucleotide that is attached to the bead for capture and isolation of the combined probe, thereby producing each oligonucleotide marker within the plurality of the oligonucleotide markers.

4. The method of claim 1, further comprising determining copy number variation of a nucleic acid sequence in the nucleic acid sample.

5. The method of claim 1, further comprising quantifying relative RNA expression levels in the nucleic acid sample.

6. The method of claim 1, further comprising performing an ELISA assay on the first oligonucleotide label molecule.

7. The method of claim 1, wherein the first oligonucleotide comprises biotin.

8. The method of claim 1, wherein the bead is magnetic.

9. The method of claim 1, further comprising concentrating the markers adjacent or in proximity to the nanopore array with a magnetic field.

* * * * *